US006312155B1

(12) United States Patent
Stool et al.

(10) Patent No.: US 6,312,155 B1
(45) Date of Patent: Nov. 6, 2001

(54) APPARATUS AND METHOD FOR ASSESSING BURN INJURY FROM FLAMMABLE MATERIALS

(75) Inventors: Daniel Stool, Addison, IL (US); Merrill Zavod, Merion, PA (US); Scott Milkovich, Glen Ellyn; Eugene D. Rider, Westchester, both of IL (US)

(73) Assignee: Risk Analysis & Management, Oak Brook, IL (US)

( * ) Notice: Subject to any disclaimer, the term of this patent is extended or adjusted under 35 U.S.C. 154(b) by 0 days.

(21) Appl. No.: 09/413,253

(22) Filed: Oct. 7, 1999

Related U.S. Application Data

(60) Provisional application No. 60/109,256, filed on Nov. 19, 1998, and provisional application No. 60/103,619, filed on Oct. 9, 1998.

(51) Int. Cl.[7] .................................................. G01K 1/16
(52) U.S. Cl. .................................. 374/45; 374/8; 374/134
(58) Field of Search .................................. 374/8, 45, 57, 374/134, 136; 600/549

(56) References Cited

U.S. PATENT DOCUMENTS 2,477,526 * 7/1949 Perley ..................................... 374/45
3,667,277 * 6/1972 Miller et al. ............................. 374/8

(List continued on next page.)

FOREIGN PATENT DOCUMENTS

0231415 * 12/1984 (JP) ........................................ 374/45
0219512 * 11/1985 (JP) ........................................ 374/45
02080919A * 3/1990 (JP) ....................................... 374/148
02122247A * 5/1990 (JP) ........................................ 374/45
10332683A * 12/1998 (JP) .

(List continued on next page.)

OTHER PUBLICATIONS

M. P. Chouinard et al., "Heat Transfer from Flammable Fabrics," *Textile Res. J.*, vol. 43, No. 3, 1973, pp. 166–175.
F. C. Henriques, Jr. et al., "Studies of Thermal Injury," *Am. J. Path.*, vol. XXIII, No. 4, Jul. 1947, pp. 531–549.
A. R. Moritz et al., "Studies of Thermal Injury," *Am. J. Path.*, vol. XXIII, No. 5, Sep. 1947, pp. 695–720.
F. C. Henriques, Jr., "Studies of Thermal Injury," *Am. J. Path.*, vol. 43, No. 6, May 1947, pp. 489–502.
M. A. Chianta et al., "Thermal Conduction Effects in Human Skin: I. Experimental Data Acquisition," Department of Navy: Naval Air Development Center, Report No. NADC–79033–60, Jan. 15, 1979.

(List continued on next page.)

*Primary Examiner*—Diego Gutierrez
*Assistant Examiner*—Lydia M. De Jesús
(74) *Attorney, Agent, or Firm*—Finnegan, Henderson, Farabow, Garrett & Dunner, L.L.P.

(57) ABSTRACT

An apparatus for assessing burn injury to underlying tissue from a flammable material. The apparatus includes an artificial human tissue and a plurality of temperature sensors located at predetermined locations in the artificial human tissue to measure temperature of the artificial human tissue during a flammability test. The apparatus further includes a heat sink device for simulating the heat sink properties of a human body. The apparatus further includes a heat exchange tank for maintaining the artificial human tissue at a regulated temperature, the heat exchange tank being filled with a fluid. The apparatus further includes a heat exchanger for exchanging heat with the fluid in the heat exchange tank. The apparatus further includes a water supply device for supplying water to the interior of the heat exchanger. The apparatus also includes a data acquisition system attached to the plurality of temperature sensors for recording the temperature of the artificial human tissue. The invention also includes a method for assessing burn injury to underlying tissue from a flammable material during a flammability test.

28 Claims, 28 Drawing Sheets

U.S. PATENT DOCUMENTS

| | | | | |
|---|---|---|---|---|
| 3,685,343 | * | 8/1972 | Cochran, II | 374/8 |
| 3,688,558 | * | 9/1972 | Tixier | 374/45 |
| 3,930,397 | * | 1/1976 | Suga | 374/8 |
| 4,309,901 | * | 1/1982 | Rolinski et al. | 73/147 |
| 4,468,135 | * | 8/1984 | McCain et al. | 374/44 |
| 5,409,382 | * | 4/1995 | Donnelly et al. | 434/267 |

FOREIGN PATENT DOCUMENTS

| | | | | |
|---|---|---|---|---|
| 372490 | * | 3/1973 | (SU) | 374/45 |
| 0405050 | * | 10/1973 | (SU) | 374/45 |

OTHER PUBLICATIONS

F. J. Kilzer et al., "Speculations on the Nature of Cellulose Pyrolysis," *Pyrodynamics*, vol. 2, No. 2–3, Mar. 1965, pp. 151–163.

R. D. Robertson et al., "Burn Injuries: A Guide to Assessment, Proven Management Approaches," *Consultant*, vol. 36, No. 9, Sep. 1996, pp. 1873–1879.

R. E. Schoen et al., "Visometric and Microcirculatory Observations Following Flame Injury," *J. Trauma*, vol. II, No. 7, Jul. 1971, pp. 619–624.

D. C. Ross et al., "An Experimental Investigation of Burn Injury in Living Tissue, " *Journal of Heat Transfer*, vol. 98, Series C, No. 2, May 1976, pp. 292–296.

D. C. Ross et al., "Therapeutic Effects of Postburn Cooling," *J. Biomech. Eng.*, vol. 100, Aug. 1978, pp. 149–152.

K. R. Diller et al., "Analysis of Alternate Models for Simulating Thermal Burns," *J. Burn Care Rehabil.*, vol. 12, No. 2, Mar./Apr. 1991, pp. 177–189.

K. R. Diller et al., "A Finite Element Model of Burn Injury in Blood–Perfused Skin," *J. Biomech. Eng.*, vol. 105, Aug. 1983, pp. 300–307.

K. R. Diller, "Development and Solution of Finite–Difference Equations for Burn Injury With Spreadsheet Software," *J. Burn Care Rehabil.*, vol. 20, No. 1, Part 1, Jan./Feb. 1999, pp. 25–32.

K. R. Diller, "Modeling Thermal Skin Burns on a Personal Computer," *J. Burn Care Rehabil.*, vol. 19, No. 5, Sep./Oct. 1998, pp. 420–429.

J. M. Cusick et al., "Children's Sleepwear: Relaxation of the Consumer Product Safety Commission's Flammability Standards," *J. Burn Care Rehabil.*, vol. 18, No. 5, Sep./Oct. 1997, pp. 469–474.

A. R. Moritz, "Studies of Thermal Injury," *Am. J. Pathol.* , vol. XXIII, No. 6, Nov. 1947, pp. 915–941.

A. R. Moritz et al., "Studies of Thermal Injury," *Archives of Pathology*, vol. 43, No. 5, May 1947, pp. 466–488.

K. Buettner, "Effects of Extreme Heat and Cold on Human Skin," *J. Physiol.*, vol. 3, No. 12, Jun. 1951, pp. 691–702.

K. Buettner, "Effects of Extreme Heat and Cold on Human Skin," *J. Physiol.*, vol. 3, No. 12, Jun. 1951, pp. 703–713.

K. Diller, "The Mechanisms and Kinetics of Heat Injury Accumulation," *Ann. NY Acad. Sci.*, vol. 720, May 31, 1994, pp. 38–55.

L. J. Hayes et al., "A Finite Element Model for Phase Change Heat Transfer in a Composite Tissue with Blood Perfusion," *ISA Transactions*, vol. 22, No. 4, 1983, pp. 33–37.

M. Turegun et al., "An Extraordinary Cause of Scalding Injury in Childhood," *Burns*, vol. 23, No. 2, 1997, pp. 170–173.

M. Hirschler et al., "Tests of the Protective Effect of Clothing in Apparel Fire," *J. Fires Sciences*, vol. 14, No. 2, Mar./Apr. 1996, pp. 104–123.

M. Momoh et al., "Effect of Flame–Retardant Treatment on the Thermal Behavior of Cotton Fabric," *Textile Research Journal*, vol. 60, No. 10, Oct. 1990, pp. 557–560.

S. J. Grayson et al., "A New International Standard for Flammability Testing," *Plastics Engineering*, Apr. 1994, pp. 29–31.

S. Backer et al., *Textile Fabric Flammability*, MIT Press, 1976, pp. 22–23, 187–190, 195.

* cited by examiner

TWILL

MATERIAL: 100% COTTON
WEIGHT: 123 g

45 DEGREE ANGLE

VERTICAL

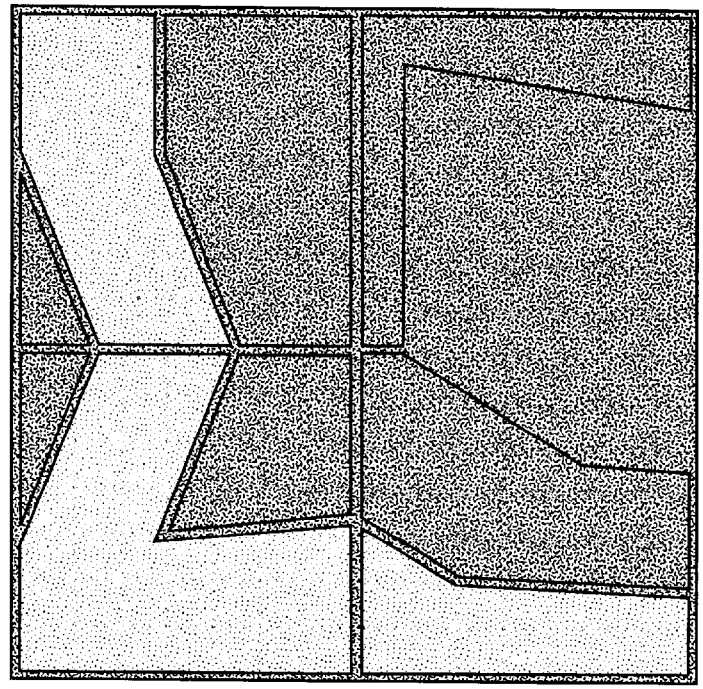

APPARATUS AND METHOD FOR ASSESSING BURN INJURY FROM FLAMMABLE MATERIALS

This application claims priority under 35 U.S.C. § 119 based on U.S. Provisional Application Serial No. 60/109,256, filed Nov. 19, 1998, and U.S. Provisional Application Serial No. 60/103,619, filed Oct. 9, 1998, the disclosures of which are incorporated by reference.

BACKGROUND OF THE INVENTION

1. Field of the Invention

This invention relates to an apparatus and method for use with a flammability test, and more particularly, to an apparatus and method for assessing burn injury to underlying tissue from flammable material.

2. Description of the Related Art

Currently, government standards exist in both the United States and the United Kingdom which require fabrics used in garments worn by children to pass a "flammability test." However, current flammability standards are inadequate.

Current flammability standards in the United States and the United Kingdom require that fabrics pass satisfactory limits of ignitability and flame spread when burned according to specific guidelines. These standards have several major shortcomings. An extremely important measure which is ignored by the current standards is the rate and the amount of heat that is released to the skin and underlying tissues as a fabric burns. It is this measure which determines the actual effects of the burning material on an individual wearing the garment. The lack of standards using heat release as a factor allows many fabrics to pass current legal standards although the fabrics are actually extremely dangerous. For example, approximately 50% of burn injuries result from fabrics which have passed the current standards. As a result of these flawed standards and tests, there is still a high incidence of severe burn injuries to children caused by their clothing catching on fire.

In the United Kingdom, the Department of Trade and Industry reports that during the period of 1991–1995, 18 injuries were the result of burns caused by children's clothing catching on fire. In addition, 5 deaths during the period of 1990–1994 in the United Kingdom were attributed to burns caused by children's clothing catching on fire (HADD, 1990–1994, LASS, HASS, 1991–1995). According to both the Consumer Product Safety Commission (CPSC) and the National Electronic Injury Surveillance System (NEISS), a large portion of the total injuries to children involving daywear are caused by burns. These two organizations report that in the United States during the period of 1991–1995, 244 total injuries were the result of burns caused by children's clothing catching on fire. Despite the presence of standard flammability tests for fabrics in the United States and the United Kingdom, there remains a high incidence of burn injuries to children caused by clothing catching on fire. Therefore, the current tests and standards must be modified in order to better screen out flammable fabrics with the highest potential to cause injury.

Attempts have been made in the past to devise improved testing equipment and standards. After the first consumer garment laws were developed in the 1950s, more stringent laws were passed in the 1960s and 1970s. These laws brought about a period of intensive research in the field of fabric flammability. In the early 1970s, a series of studies were carried out which attempted to quantify the amount of heat released from fabrics during burning. However, these studies proved to be inadequate in modeling the amount of heat released to the underlying skin from burning fabric. These studies did not adequately mimic the thermal properties of the skin and underlying tissues. Since the 1970s, however, there has been very little fire-related literature, largely as result of a decrease in funds for research.

Therefore, there is a need for an apparatus and method for assessing burn injury to underlying tissue from a flammable material which will also measure the heat released to the underlying tissue.

SUMMARY OF THE INVENTION

The advantages and purposes of the invention will be set forth in part in the description which follows, and in part will be obvious from the description, or may be learned by practice of the invention. The advantages and purposes of the invention will be realized and attained by means of the elements and combinations particularly pointed out in the appended claims.

To attain the advantages and in accordance with the purposes of the invention, as embodied and broadly described herein, the invention includes an apparatus for assessing burn injury to underlying tissue from a flammable material. The apparatus includes an artificial human tissue and a plurality of temperature sensors located at predetermined locations in the artificial human tissue to measure temperature of the artificial human tissue during a flammability test.

In another aspect, the apparatus further includes a heat exchange tank for maintaining the artificial human tissue at a regulated temperature, the heat exchange tank being filled with a fluid. The artificial human tissue is mounted in an opening in the heat exchange tank and contacted on an interior surface by the fluid. The apparatus further includes a heat exchanger for exchanging heat with the fluid in the heat exchange tank to maintain the fluid of the exchange tank at the regulated temperature. The apparatus further includes a water supply device for supplying water to the interior of the heat exchanger. The water supply device includes a water tank, a pump, and a heater. The apparatus also includes a data acquisition system attached to the plurality of temperature sensors for recording the temperature of the artificial human tissue.

In a further aspect of the invention, the invention includes a method for assessing burn injury to underlying tissue from a flammable material during a flammability test. The method comprises the steps of mounting a piece of flammable material in a standard flammability test frame at a selected distance from an artificial human tissue located on a test apparatus, circulating a fluid through the test apparatus at a temperature substantially the same as ordinary human skin temperature, performing the flammability test, and recording temperatures of the artificial human tissue at a plurality of locations over predetermined intervals during the flammability test.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention. In the drawings.

FIGS. 29–32 are burn maps for a variety of materials.

DESCRIPTION OF THE PREFERRED EMBODIMENTS

Reference will now be made in detail to the present preferred embodiments of the invention, examples of which are illustrated in the accompanying drawings. Wherever possible, the same reference numbers will be used throughout the drawings to refer to the same or like parts.

In accordance with the present invention, an apparatus is provided for assessing burn injury to underlying tissue from a flammable material. The apparatus is generally comprised of an artificial human tissue, a plurality of temperature sensors located in the artificial human tissue, a heat sink device for simulating the heat sink properties of a human body, and a data acquisition system. The apparatus may be used in conjunction with a flammability test. The apparatus is compatible for use with a sample holder used in standard flammability tests, or other suitable sample holders.

Figure 1:
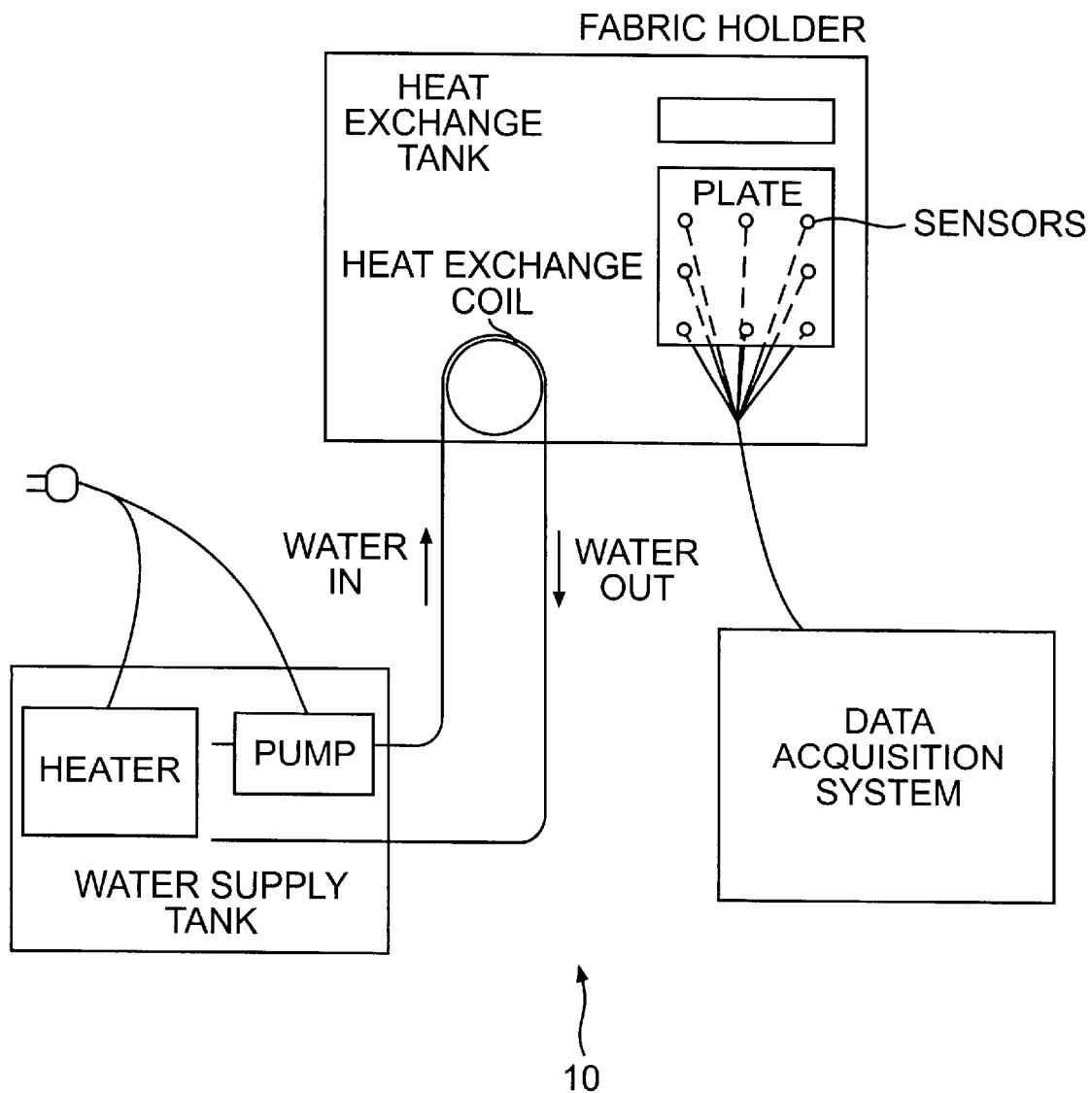
FIG. 1 is a schematic diagram of an apparatus for assessing burn injury according to a first embodiment of the invention.

FIG. 1 illustrates a general schematic of the apparatus, the details of which will be disclosed in the accompanying drawings and remainder of the specification. A heat exchange tank is provided with a sensor plate on its outside surface. A fabric sample holder is mounted above the sensor plate for holding a sample of flammable material to be burned. The heat exchange tank contains a first fluid and a heat exchange coil. Water is circulated from a water supply tank through the heat exchange coil. The water supply tank is provided with a pump for supplying the water to the heat exchange tank, and a heater for maintaining the temperature of the water in the water supply tank at a set temperature. The sensor plate on the heat exchange tank is provided with a plurality of sensors on the inside surface. Measurements from the sensors are then fed to a data acquisition system so that calculations can be made.

Figure 23:
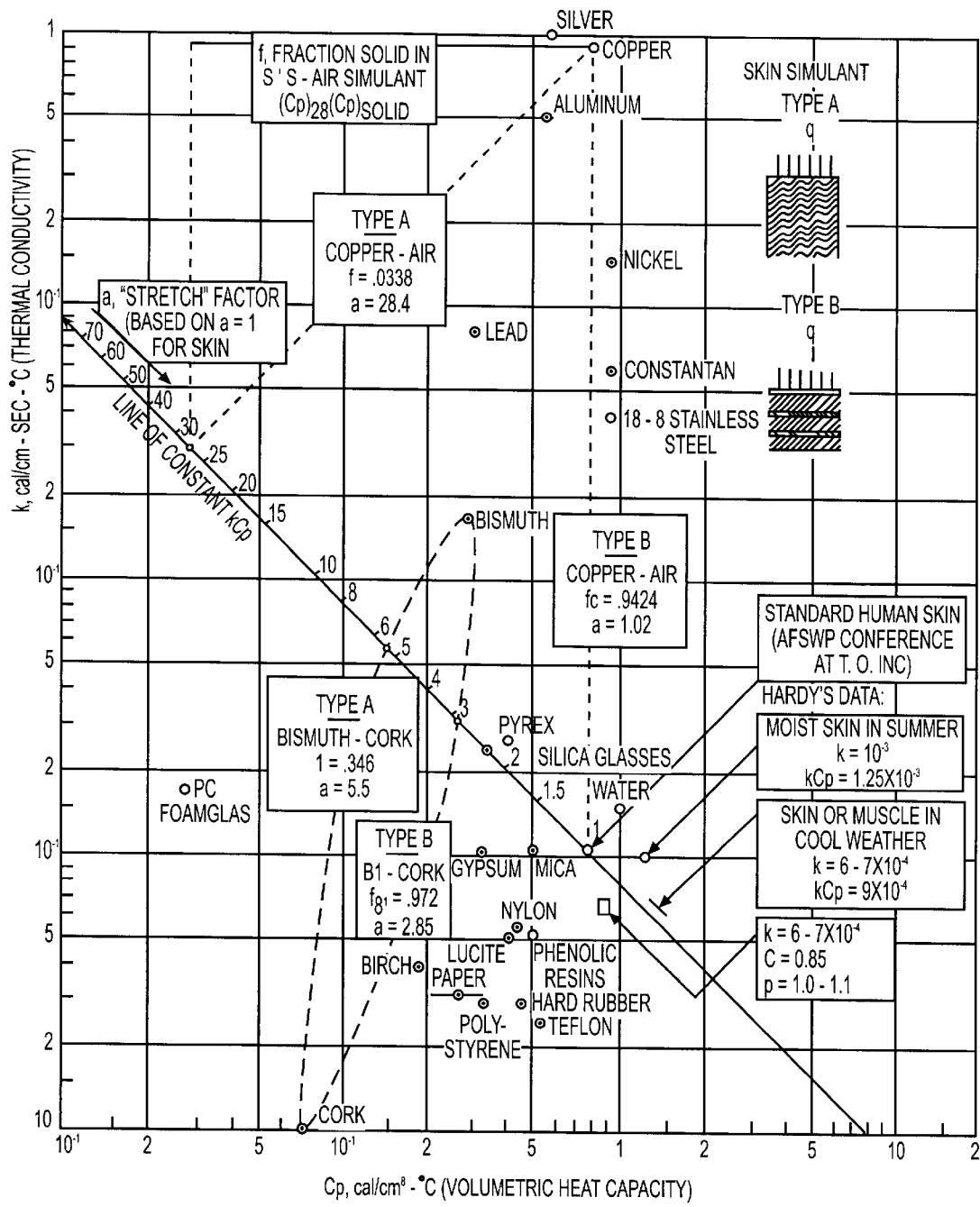
FIG. 23 is a graph of the thermal conductivity vs. volumetric heat capacity for a variety of materials.

In accordance with the present invention, the apparatus includes an artificial human tissue, for example, artificial human skin. Although artificial human skin is preferred, the invention encompasses other artificial human tissues. The exemplary embodiment of the apparatus will be described below with reference to FIGS. 2–10. As embodied herein and shown in FIGS. 2, 3, 5, and 7–8, apparatus 10 includes an artificial human skin 28 in the form of a sensor plate. The sensor plate 28 is composed of a material having thermal properties similar to that of ordinary human skin. The sensor plate material closely mimics the thermal properties of human skin, but does not break down or ignite during the burning process. In the exemplary embodiment, sensor plate 28 is a thin rectangular sheet of mica material. It is to be understood that other materials which have properties similar to human skin or other human tissue also may be used. FIG. 23 shows a series of different materials on a chart according to the properties of thermal conductivity and volumetric heat capability. Mica was selected because it most closely approximates the thermal properties of human skin and can withstand the high temperatures associated with fabric burning.

In accordance with the present invention, a plurality of temperature sensors are located at predetermined locations in the artificial human tissue to measure temperature of the artificial human tissue during the flammability test. Although the invention preferably uses thermocouples, other temperature sensors may be used instead. As embodied herein and shown in FIGS. 1–3 and 7, the apparatus 10 includes a plurality of thermocouples 32. The thermocouples 32 are embedded in holes 30 in the bottom surface of sensor plate 28. The holes 30 are drilled in the bottom surface of the sensor plate 28, but do not completely pass through the sensor plate. For instance, in a preferred embodiment, the holes may be drilled so that there is approximately 1 mm between the end of the hole and the top surface of the sensor plate. By not exposing the thermocouples directly to the flame, the thermocouples measure the temperature of the artificial human tissue and not the temperature of the flame. The thermocouples 32 may be secured in the holes by a variety of methods. In the illustrated embodiment, as best shown in FIG. 3, the thermocouples are dipped in high temperature epoxy 31 and inserted in the holes 30.

Figure 7:
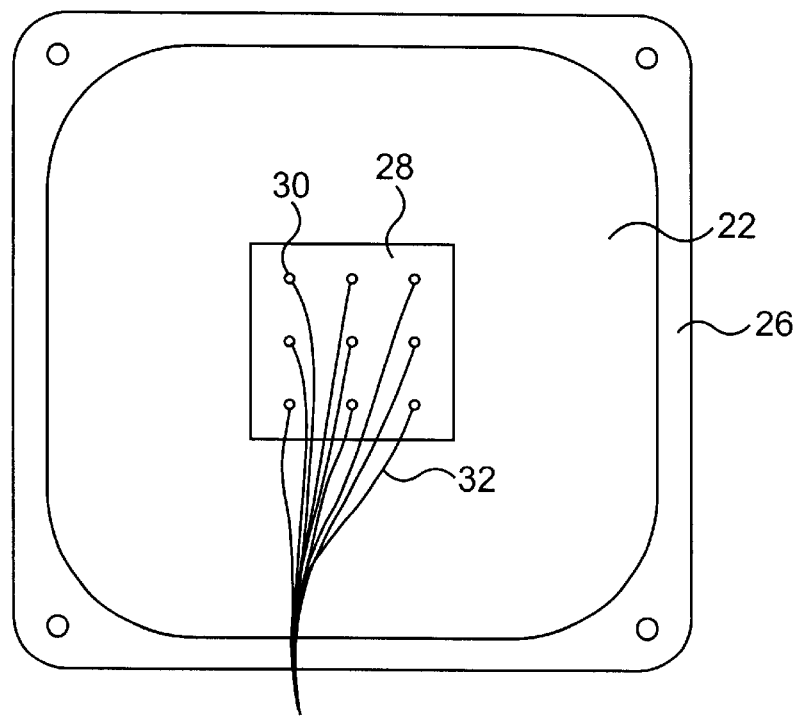
FIG. 7 is a bottom view of the inside of a pan of the apparatus of FIG. 2.
Figure 8:
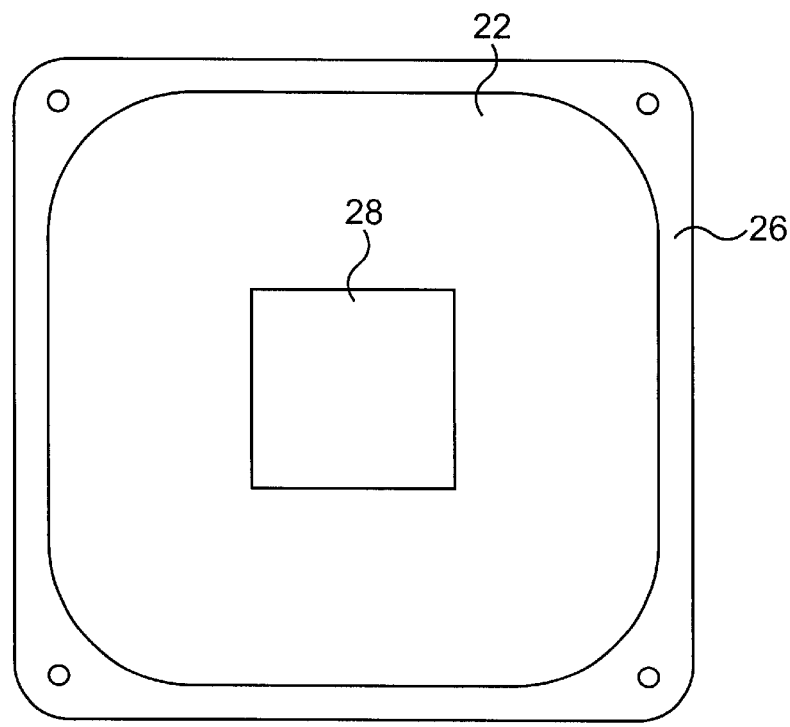
FIG. 8 is a top view of the outside of the pan of the apparatus of FIG. 2.

The sensor plate may have any number of holes for thermocouples. In the illustrated embodiment, the sensor plate has 8 thermocouple holes, as best shown in FIG. 7. The provision of multiple thermocouples allows for analysis of the pattern of burning from a given fabric. The thermocouples 32 measure the temperatures at each location of the sensor plate simultaneously at predetermined intervals.

In accordance with the present invention, the apparatus includes a heat sink device for simulating the heat sink properties of a human body. As embodied herein and shown in FIGS. 1–8, sensor plate 28 is located on the top portion of a heat exchange tank or container 18, as best shown in FIG. 3. In the illustrated embodiment, container 18 includes a rectangular pan 20 having a top surface 22, side surfaces 24, and bottom flanges 26. Sensor plate 28 is located in an opening in the top surface of pan 20. As shown in FIG. 3, the sensor plate 28 is located on a shaved mount surface 23 of the top surface of the pan. In the illustrated embodiment, the sensor plate 28 is fixed to the shaved mount surface 23 of the pan by use of high temperature epoxy. The sensor plate may be attached to the shaved mount surface 23 by any other suitable method, such as the use of bolts or other conventional fasteners. In addition, the sensor plate 28 can be located in a variety of different positions, such as on the inside of the top surface 22, or could take up the entire top surface 22 of the container.

Figure 3:
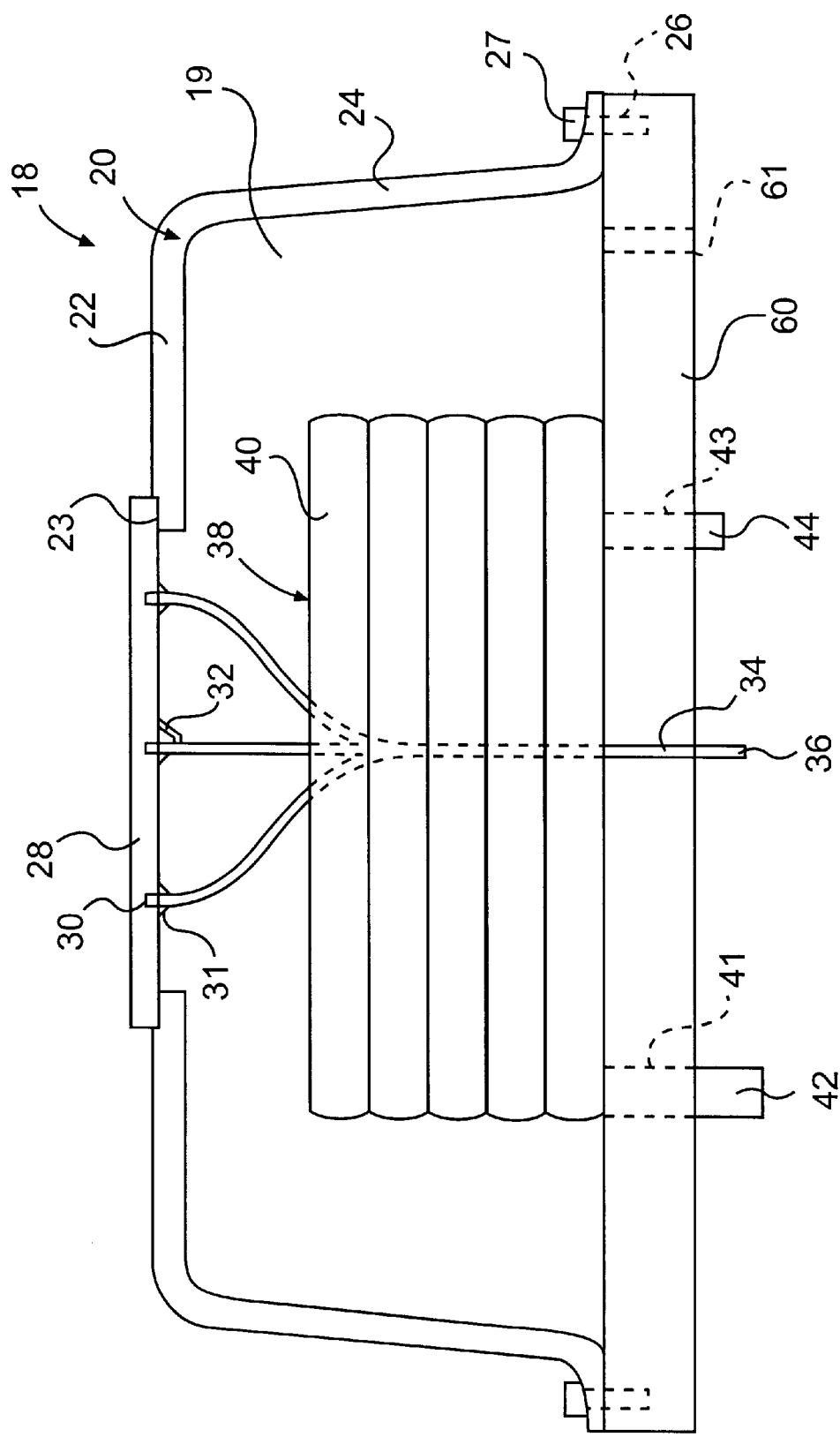
FIG. 3 is a partial cross-section of a container of the apparatus of FIG. 2.
Figure 9:
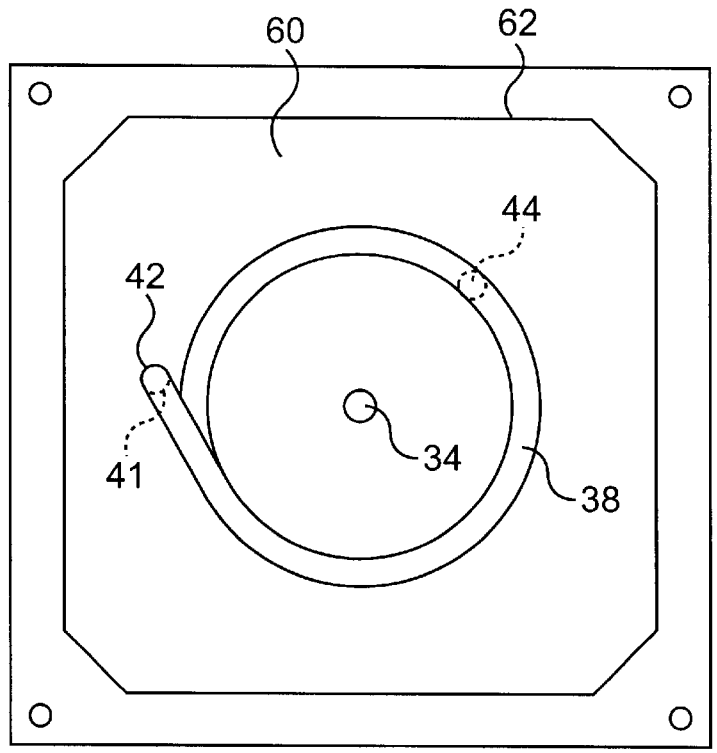
FIG. 9 is a top view of a bottom plate and heat exchange coil with the pan removed in the apparatus of FIG. 2.
Figure 10:
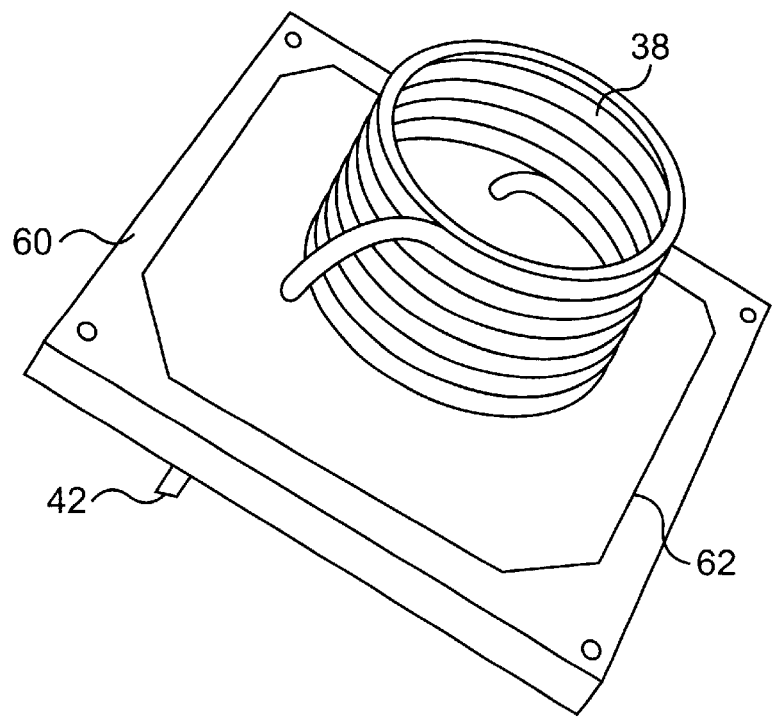
FIG. 10 is a perspective view of the bottom plate and heat exchange coil with the pan removed in the apparatus of FIG. 2.
Figure 11:
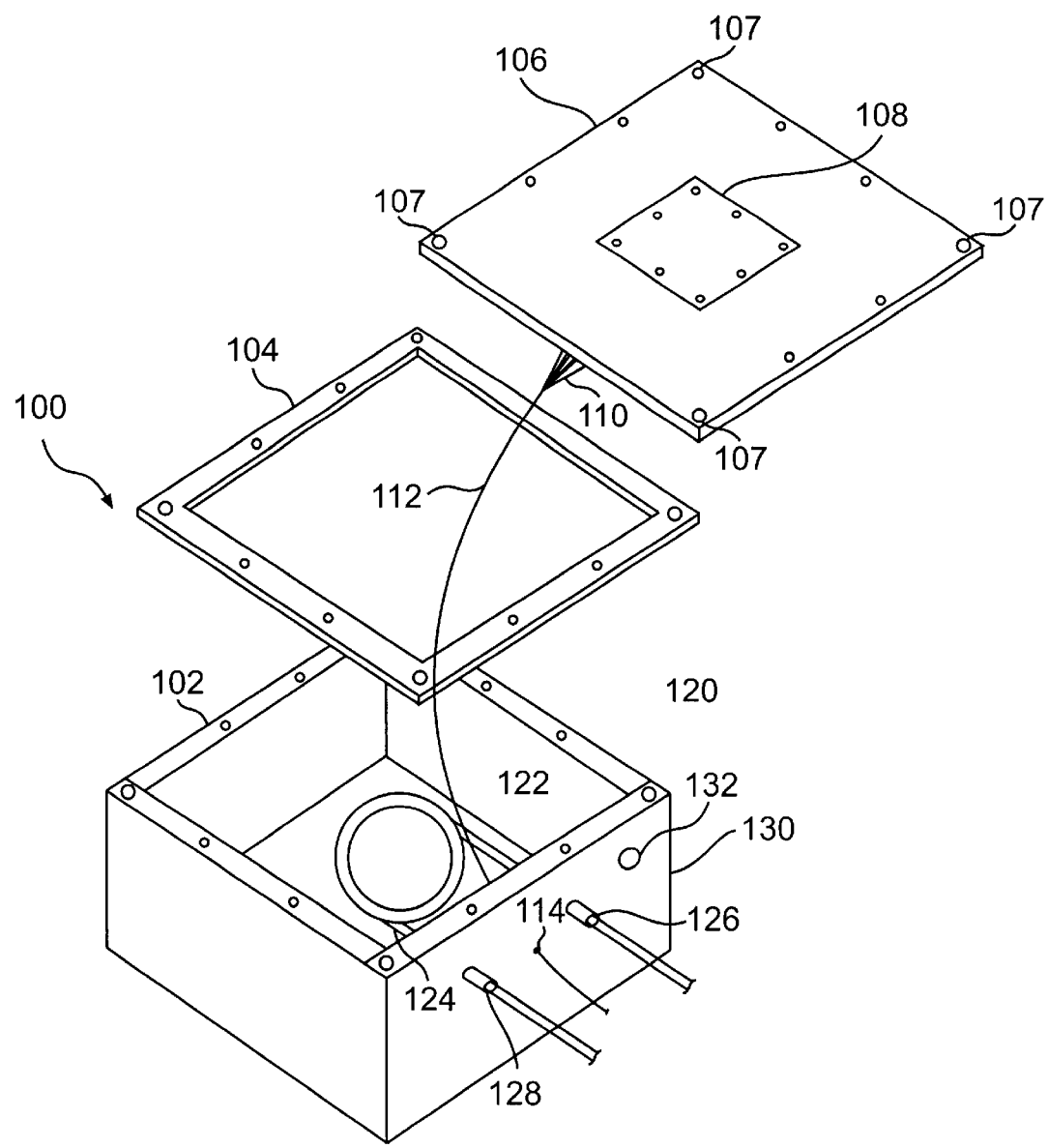
FIG. 11 is a perspective view of an unassembled container according to a second embodiment of the invention.

In the illustrated embodiment, container 18 also includes a bottom support plate 60, as best shown in FIGS. 3, 9 and 10. Bottom support plate 60 is a flat rectangular plate which is sized to fit the dimensions of the bottom flange 26. The pan 20 is mounted on the bottom support plate through bolts 27 passing through the bottom flange 26 or by any other acceptable method. An o-ring 62 is positioned between the pan 20 and the bottom support plate 60. O-ring 62 is affixed into a groove formed in the bottom support plate, using conventional fixing means such as glue or another adhesive. The o-ring 62 and any other acceptable sealant are provided in order to prevent leakage of the fluid contained in the container. The bottom plate is provided with thermocouple hole 34 for passage of the bundled thermocouples 32 through the bottom plate to a data acquisition system 56. In the illustrated embodiment, hole 34 is provided in the center of the bottom plate.

In the illustrated embodiment, container 20 is filled with a fluid 19. The fluid is typically water, however, other fluids also could be used. The water in the pan remains within the container and does not circulate to other portions of the apparatus. The water is placed into the container via port holes 61 located in the bottom support plate 60. The port holes are then filled by plugs in order to prevent loss of the water. As shown in FIG. 3, the water in the container is in contact with the bottom surface of the sensor plate 28. The water serves as a heat sink for mimicking the heat sink characteristics of the human body. The water will absorb heat from the burning fabric in a manner similar to that of the human body.

In accordance with the present invention, the heat sink device further includes a heat exchanger for exchanging heat with the fluid in the container. Also in accordance with the present invention, a supply system is provided for supplying a second fluid to the heat exchanger.

As embodied herein and as shown in FIGS. 2, 3 and 9–10, heat exchanger 38 is provided in the container 18. The heat exchanger 38 preferably is in the form of a heat exchange coil made of aluminum tubing 40, as best shown in FIGS. 3, 9 and 10. Fluid enters the coil at first end 42, circulates through the circular coil and exits at second end 44. The heat exchange tubing 40 is generally wrapped so that the coil is substantially parallel to the bottom plate. Holes 41 and 43 are provided in the bottom support plate for first and second coil ends 42 and 44 respectively. The heat exchange coil 38 is mounted on the top surface of bottom support plate 60. Although the illustrated embodiments show a heat exchanger in the form of a coil, any other type of heat exchanger may be utilized, for example, a plate heat exchanger, a tube heat exchanger, or a heater inserted directly into the container. In addition, the heat exchanger may be made out of any suitable material.

Figure 2:
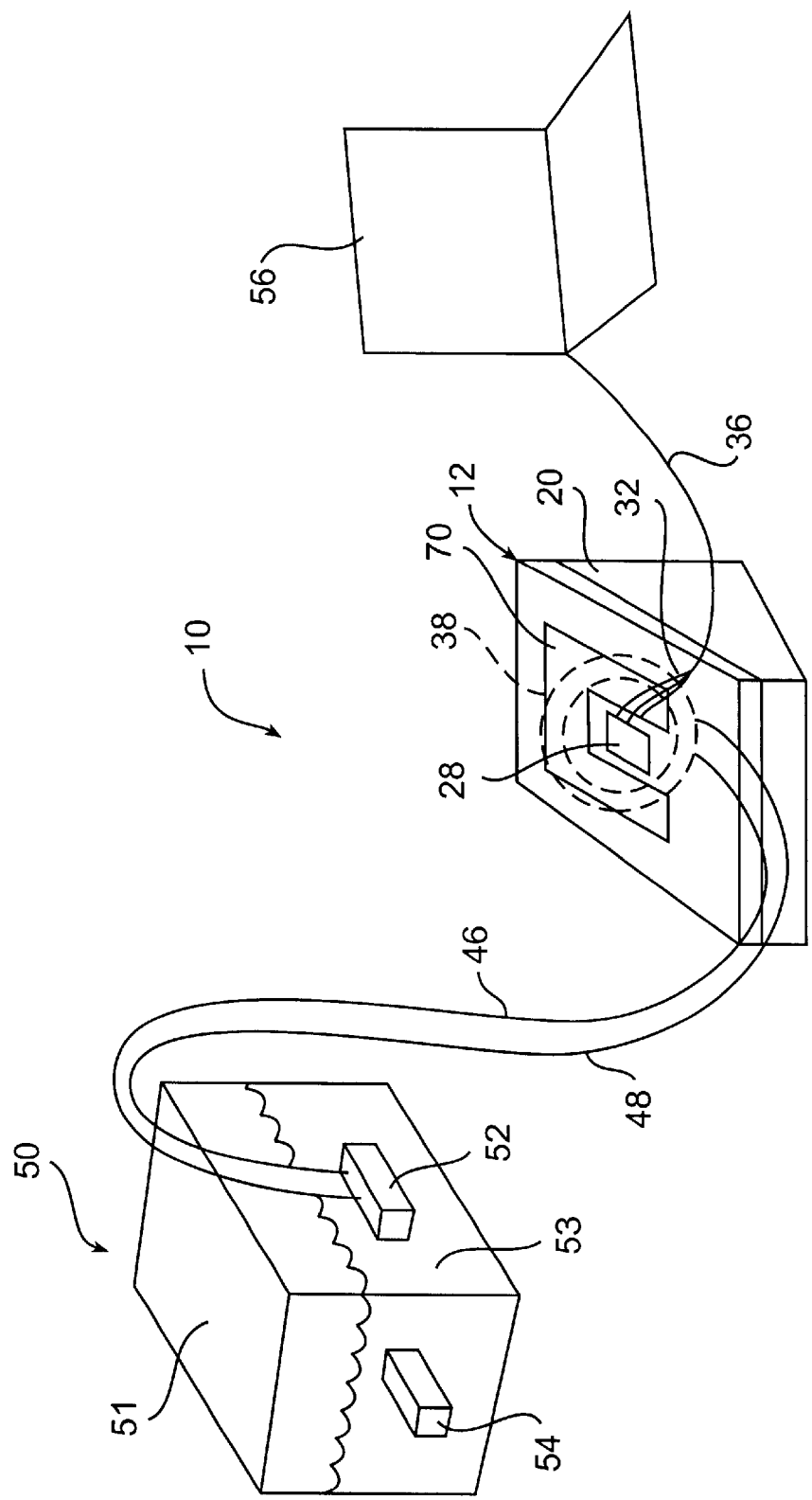
FIG. 2 is a perspective simplified view of the apparatus according to the first embodiment of the invention.

In accordance with the present invention, the apparatus includes a fluid supply system for supplying fluid to the interior of the heat exchanger. As embodied herein and shown in FIGS. 1–2, the apparatus 10 includes a fluid supply system 50. The fluid supply system 50 includes a fluid tank 51, a heater 54 and a pump 52, as best shown in FIGS. 1 and 2. Fluid tank 51 contains a reservoir of fluid 53 which may be water or any other suitable fluid. Pump 52 pumps fluid 53 from the fluid tank 51 through flexible tubing 46, through heat exchange coil 38, and back to the fluid tank 51 via flexible tubing 48. The heater serves to maintain the fluid 53 in the heat exchange coil 38 at human skin temperature. Although the core body temperature is typically 98.6 deg. F., the typical human skin temperature is less than the core body temperature. The typical human skin temperature is approximately 89.9 deg. F., therefore the fluid 53 in the heat exchange coil is preferably maintained at 89.9 deg. F. The fluid 53 circulates in the heat exchange coil and exchanges heat with the fluid 19 in the container 20.

In accordance with the present invention, the apparatus further includes a data acquisition system attached to the plurality of temperature sensors for recording the temperature of the artificial human tissue. As embodied herein and shown in FIG. 2, the data acquisition system 56 records the temperature readings from the thermocouples 32 located on the bottom surface of the sensor plate 28. In the illustrated embodiment, the data acquisition system is in the form of a laptop computer, but any other type of data acquisition system is also acceptable. The data acquisition system is capable of recording the temperature of a large number of thermocouples simultaneously.

Figure 4:
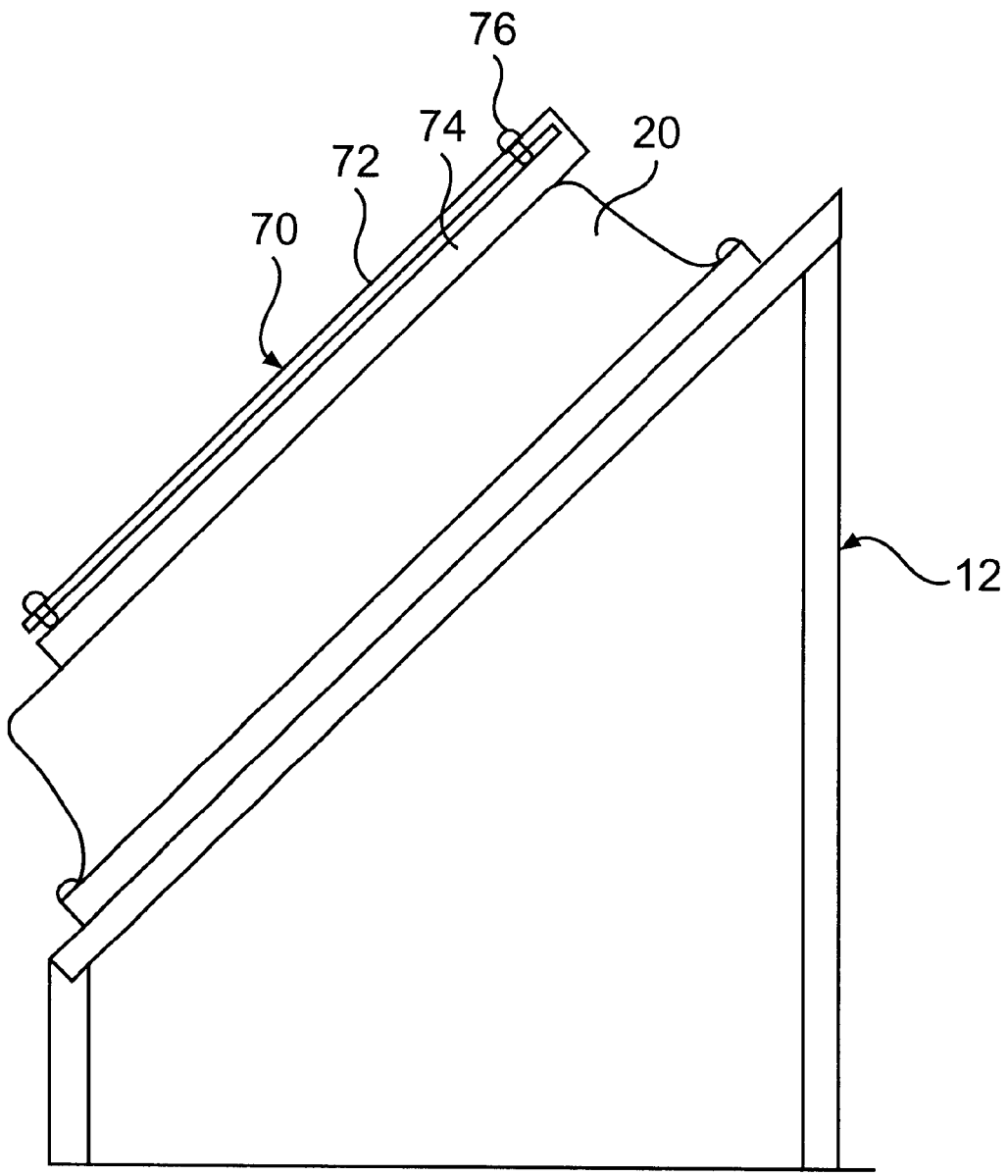
FIG. 4 is a side view of a container frame of the apparatus of FIG. 2.
Figure 5:
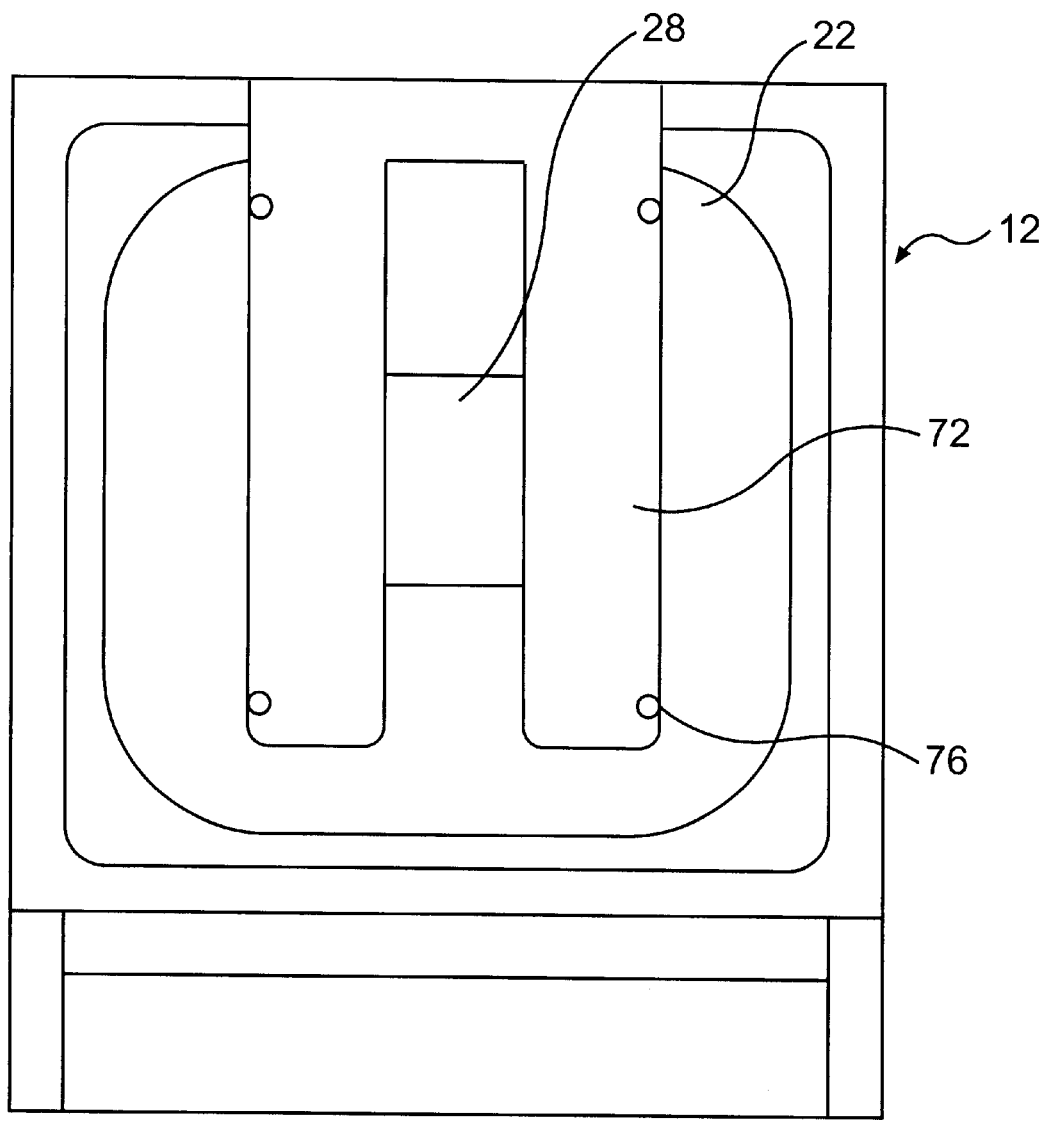
FIG. 5 is a front view of the container frame of the apparatus of FIG. 2.
Figure 6:
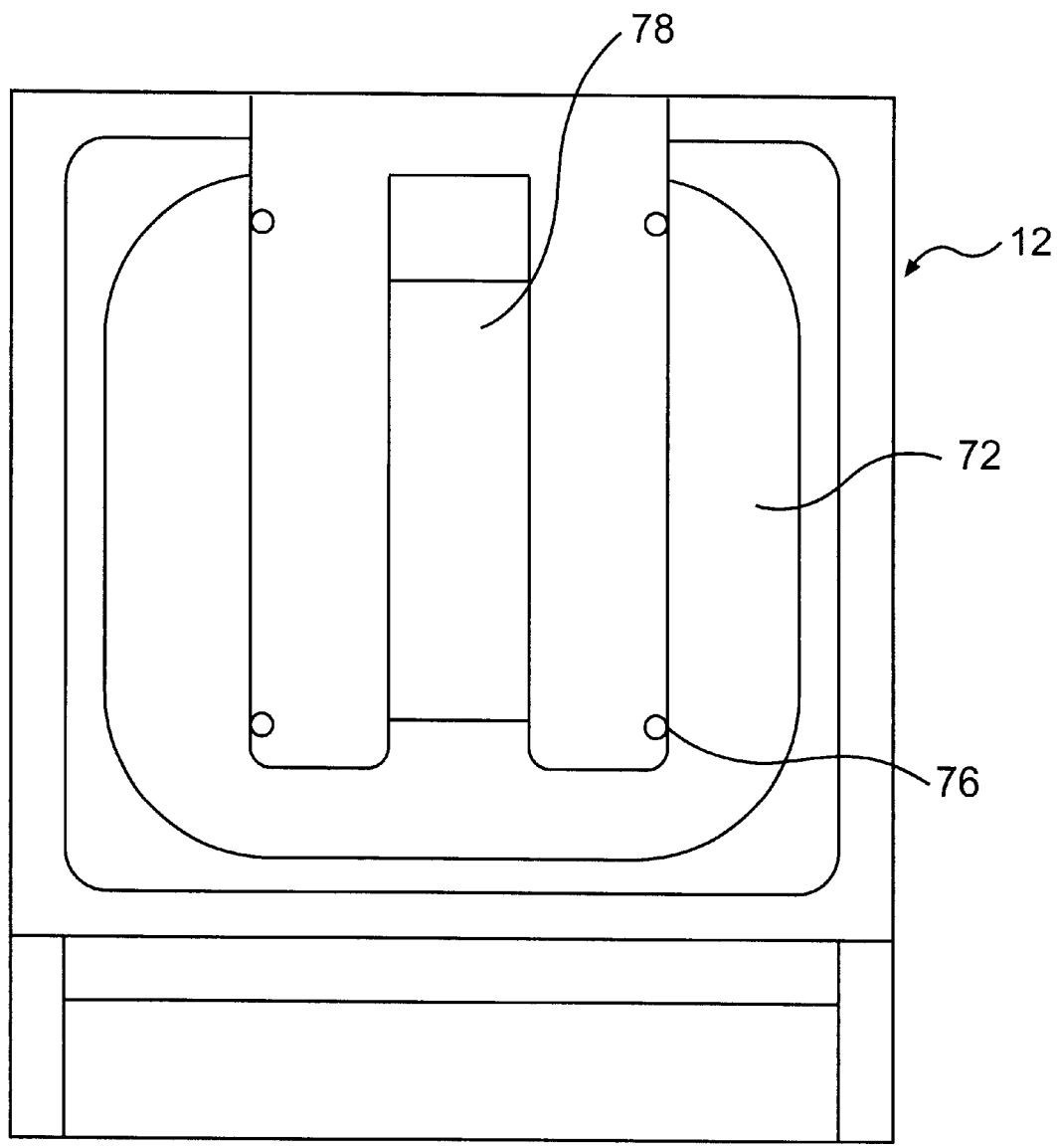
FIG. 6 is a front view of the container frame of the apparatus of FIG. 2 with a fabric sample attached.

In the illustrated embodiment of FIGS. 2–10, the container 20 is mounted in a container frame 12. The container frame can be any frame which supports a container. In the illustrated embodiment, container frame 12 is an artificial transparent material frame, e.g., PLEXIGLASS™ with a supporting base and legs. A fabric sample holder 70 is mounted on the top of the container. One type of fabric sample holder is shown in FIGS. 4–6. There are a large variety of different types and designs for sample holders, all of which are compatible with the apparatus of the present invention. The sample holder can be designed in order to duplicate the standard United States or British tests. For example, in the apparatus shown in FIGS. 4–6, fabric sample holder 70 is consistent with the sample holder used in standard U.S. flammability testing. Fabric sample holder 70 holds fabric sample 78 so that the fabric is at a standard 1 cm distance from the sensor plate during testing. The fabric sample holder can also be designed so that the fabric is at a different predetermined distance from the sensor plate.

The fabric sample holder 70 can be mounted on the front of the container or frame by any conventional method. In the embodiment shown in the FIGS. 2–10, the fabric sample holder 70 is affixed to the container by the use of thermal epoxy. As shown in FIGS. 4–6, sample holder 70 includes top plate 72 and bottom plate 74 for clamping around a fabric sample. The sample of fabric 78 or other material is squeezed between the top plate 72 and bottom plate 74. The top plate 72 and bottom plate are brought together by any type of attachment device such as a bolt 76. Other types of attachment devices include clamps for the top and bottom plates.

Another type of fabric sample holder which is suitable for the present invention is an adjustable fabric sample holder which allow for adjustments in the spacing between the sensor plate and the fabric. An example of an acceptable adjustable fabric sample holder consistent with the present invention will be described below in the discussion on FIGS. 16–17. The provision of adjustable spacing allows for evaluation of the effects of spacing a fabric from the human skin on the resulting burn injury.

In the illustrated embodiment shown in FIGS. 2–10, the fabric sample 78 is mounted at a 45 degree angle to the horizontal. This is the angle currently being used in standard flammability testing in the United States. The fabric sample could easily be placed at a different angle in the container frame by mounting the container at a different angle in the container frame.

A second embodiment of the invention will now be described wherein like or similar parts are identified throughout the drawings by the same reference characters. In particular, the changes relative to the first embodiment are directed toward the container, heat exchanger, and sensor plate. The remainder of the apparatus is essentially the same as that disclosed in the first embodiment.

Figure 14:
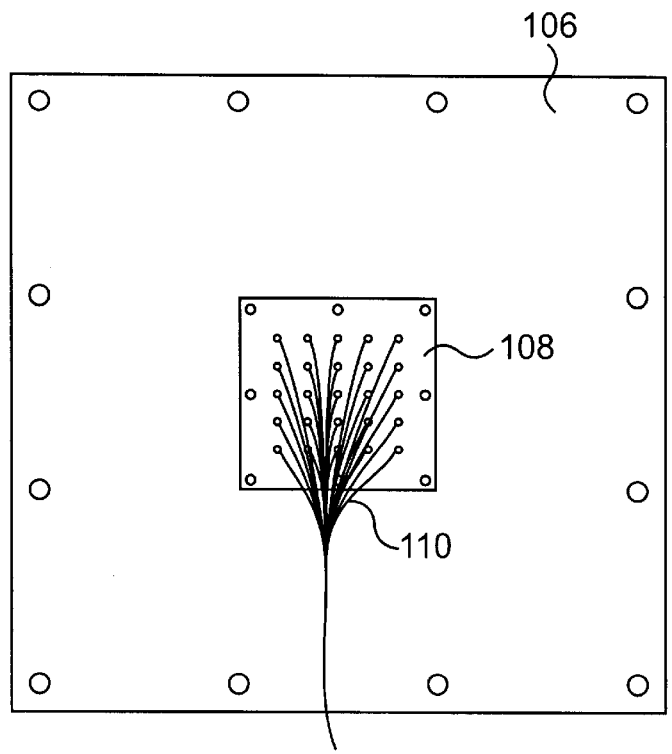
FIG. 14 is a bottom view of the top plate of the apparatus of FIG. 11.
Figure 15:
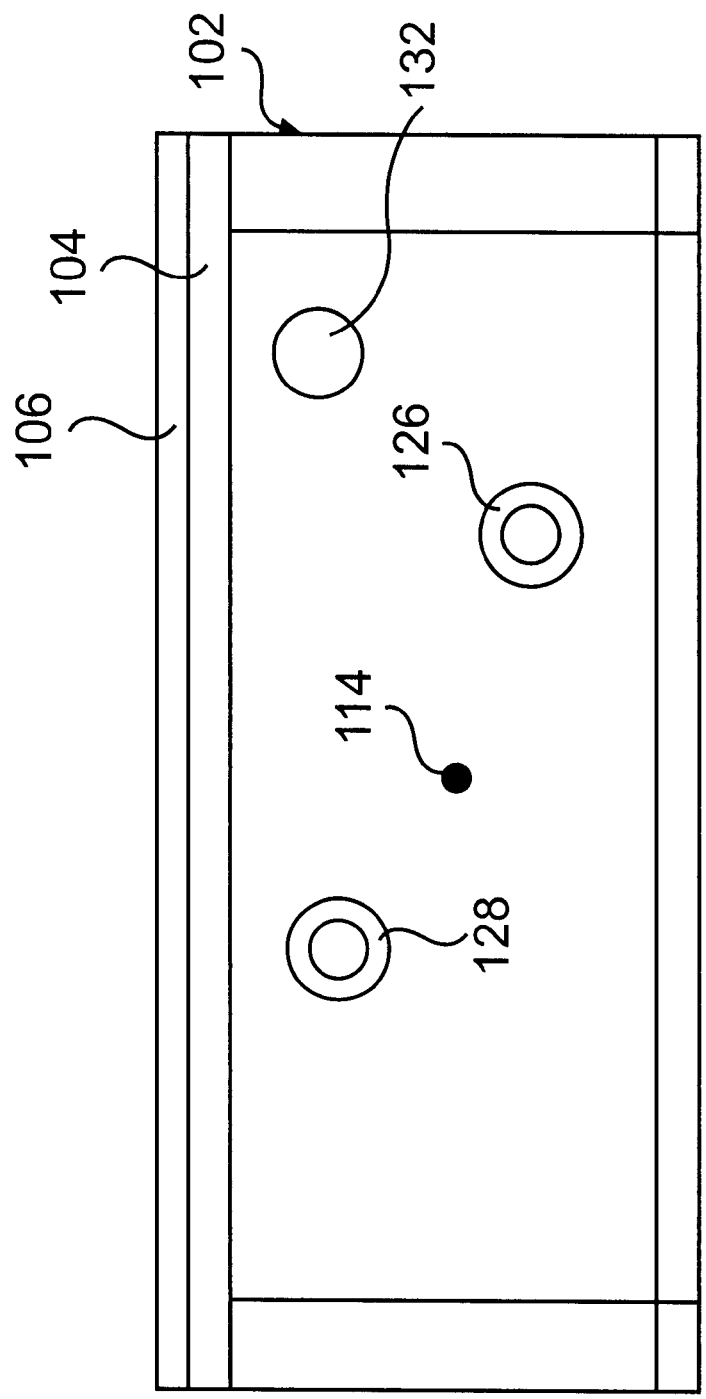
FIG. 15 is a side view of a side wall of the apparatus of FIG. 11.

In the second embodiment, which is illustrated in FIGS. 11–15, the same general principles apply as in the first embodiment. The structure, however, is slightly different. As embodied herein, the container 100 includes base 102, gasket plate 104, top plate 106, and sensor plate 108. The sensor plate 108 is similar to that used in the first embodiment, however, a different number of thermocouples may be used. As shown in FIG. 14, the sensor plate has twenty-five thermocouples 110 mounted in a 5 by 5 matrix on the bottom surface. The sensor plate 108 is mounted on a top plate 106. The sensor plate 108 may be mounted to the top plate by a variety of methods, including the use of bolts and high temperature epoxy. The top plate is preferably made of stainless steel, however other suitable materials may be used. Top plate 106 includes sample holder attachment holes 107 located on the corners of the top plate. In the illustrated embodiment, four sample holder attachment holes 107 are provided.

A gasket plate 104 is provided between the top plate 106 and the base 102. The gasket plate is preferably made of flexible graphite, however other suitable materials may be used. The top plate 106 is bolted to the base 102 by bolts or other suitable fasteners. In the illustrated embodiment, a plurality of bolt holes are provided in the top of the top plate, the gasket plate and the base. The base 102 is preferably made of plexiglass, however other suitable materials may be used. The walls and bottom of the base can be attached by a variety of methods. In the example shown, the walls are attached by silicone caulking and screws.

Figure 12:
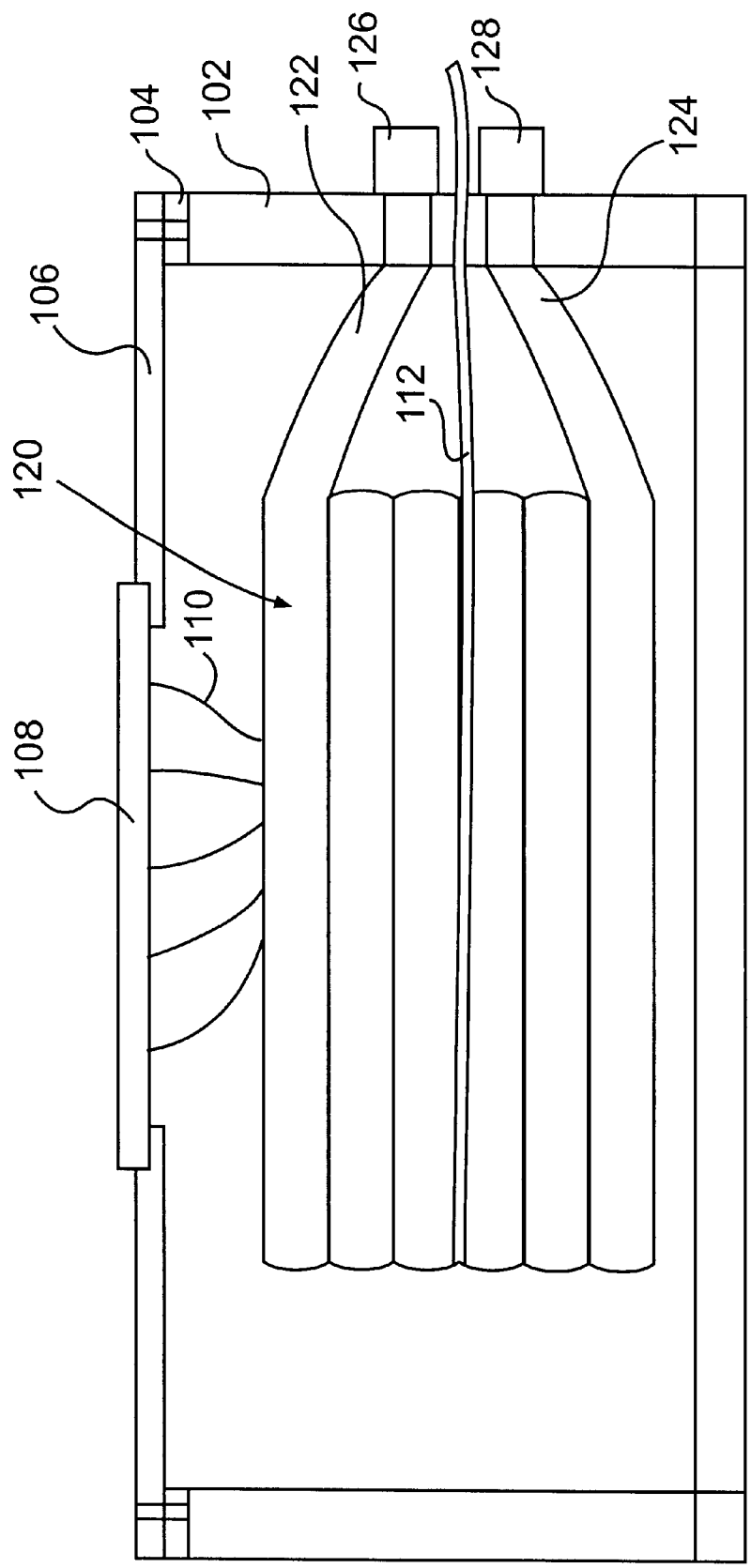
FIG. 12 is a partial cross-section of the container of the apparatus of FIG. 11.
Figure 13:
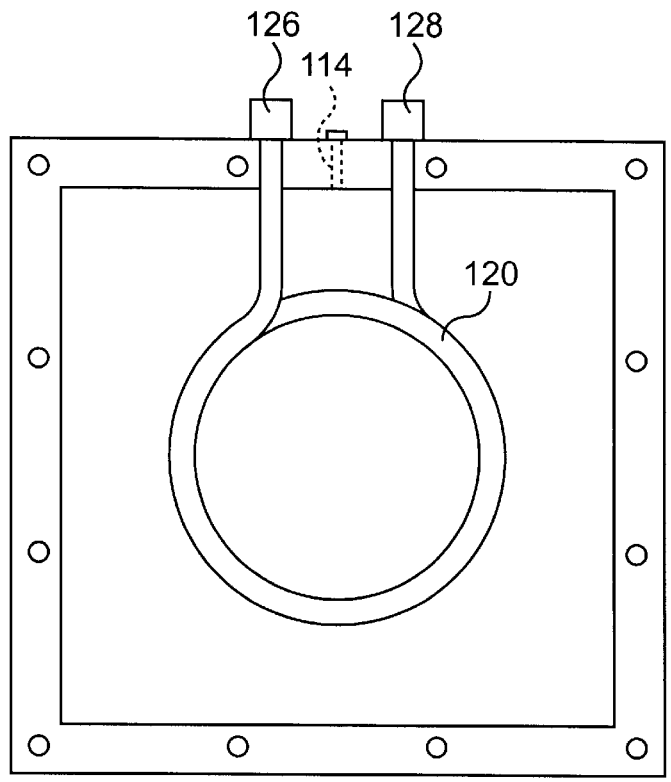
FIG. 13 is a top view of the container with a top plate removed of the apparatus of FIG. 11.

In the illustrated second embodiment, a heat exchanger is provided in the container 100. The heat exchanger in this embodiment is in the form of a heat exchange coil 120. The heat exchange coil 120 is slightly different from the heat exchange coil of the first embodiment. The heat exchange coil 120 has an inlet tube end 122 and an outlet tube end 124 that passes through a side wall 130 of the base 102. The heat exchange coil 120 has several loops. The side wall 130 also includes a thermocouple hole 114 for passing the bundled thermocouples 112 through the side wall to the data acquisition system. The thermocouples may pass through the center of the coil and then in between two adjacent loops as shown in FIG. 12. The side wall also includes a port hole 132 for filling the container with fluid. It should be understood that the size, shape and arrangement of the heat exchanger may be varied from the design shown in the second embodiment.

In the illustrated second embodiment, the remainder of the apparatus is essentially identical to the first embodiment. The same fluid supply tank and data acquisition system can be provided. The container of the second embodiment may be mounted in the same container frame as the first embodiment, or alternately in any other type of container frame.

Figure 16:
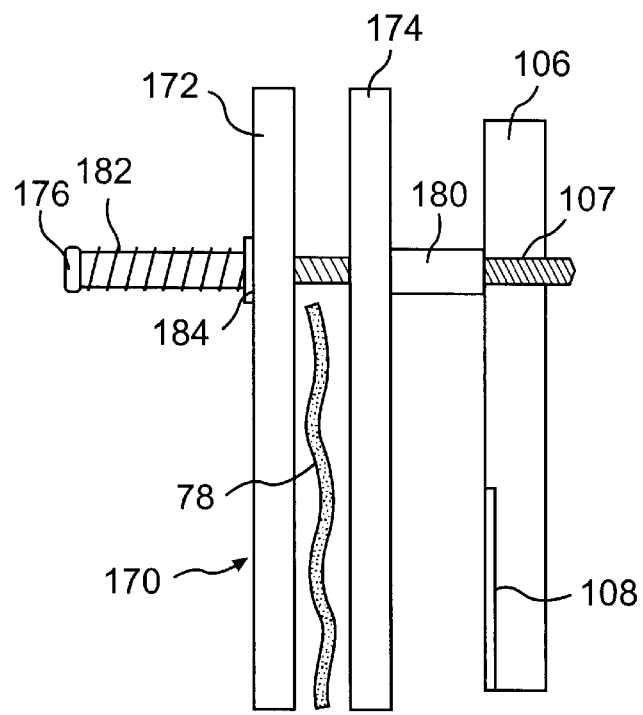
FIG. 16 is partial cross-section of a sample holder for adjusting the distance between the sample and the sensor plate.
Figure 17:
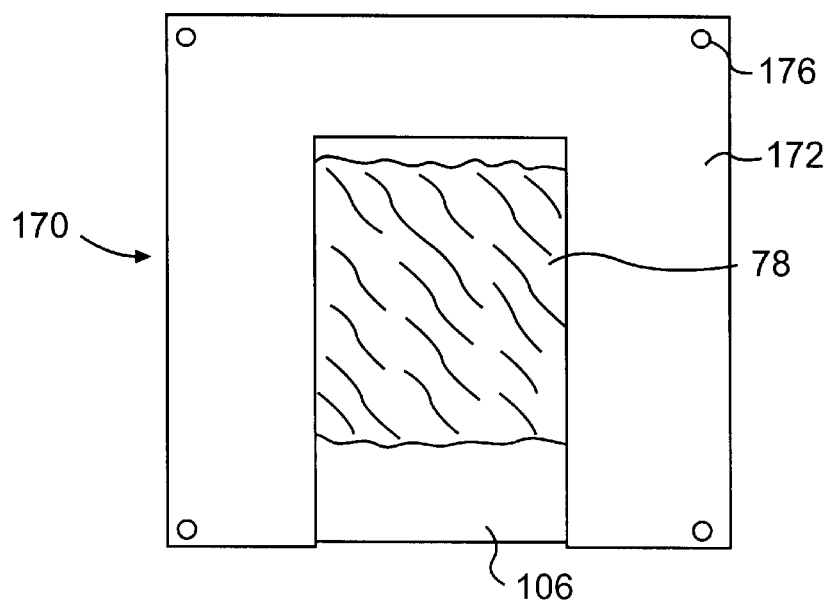
FIG. 17 is a front view of the sample holder of FIG. 16.

In accordance with the present invention, the sample holder may be provided so that the distance between the fabric sample and the sensor plate may be adjusted. An example of a type of sample holder arrangement allowing adjustability of the distance between the fabric sample and sensor plate is shown in FIGS. 16–17. An embodiment of the sample holder with adjustable spacing will be described in relation to the apparatus of the second embodiment, however, it should be understood that the adjustable sample holder is also adaptable for use with the apparatus of the first embodiment.

As embodied herein and shown in FIGS. 16–17, a sample holder 170 with adjustable spacing between the fabric sample 78 and the sensor plate 108 is provided. FIG. 16 shows the sample holder 170 prior to fabric sample 78 being fully squeezed between top sample holder plate 172 and bottom sample holder plate 174. The top sample holder plate 172 and bottom sample holder plate 174 are brought in contact with the fabric sample 78 by threading bolt 176 into sample holder attachment holes 107 in the top surface of top plate 106. A spacer 180 is provided between the bottom surface of bottom sample holder plate 174 and the top surface of top plate 106. Spacer 180 is shown as a cylinder, but could be other shapes such as square. The threaded bolt 176 threads into the threads in the sample holder attachment holes 107, therefore, threads are not provided in the inside of the spacers 180. A compression spring 182 is positioned between the head of bolt 176 and a washer 184. The washer 184 is positioned to abut the top surface of the top sample holder plate 172.

The provision of spacers allow the flammability tests to be performed with a variety of distances between the sensor plate and the fabric sample. All that is required to vary the distance between the sensor plate and fabric sample is to remove the four bolts 176 and replace the spacers 180 with different spacers with a different length than the spacers that were replaced. It should be understood that the adjustable sample holder shown in FIGS. 16–17 is also suitable for use in the apparatus of the first embodiment with minor variations.

Figure 18:
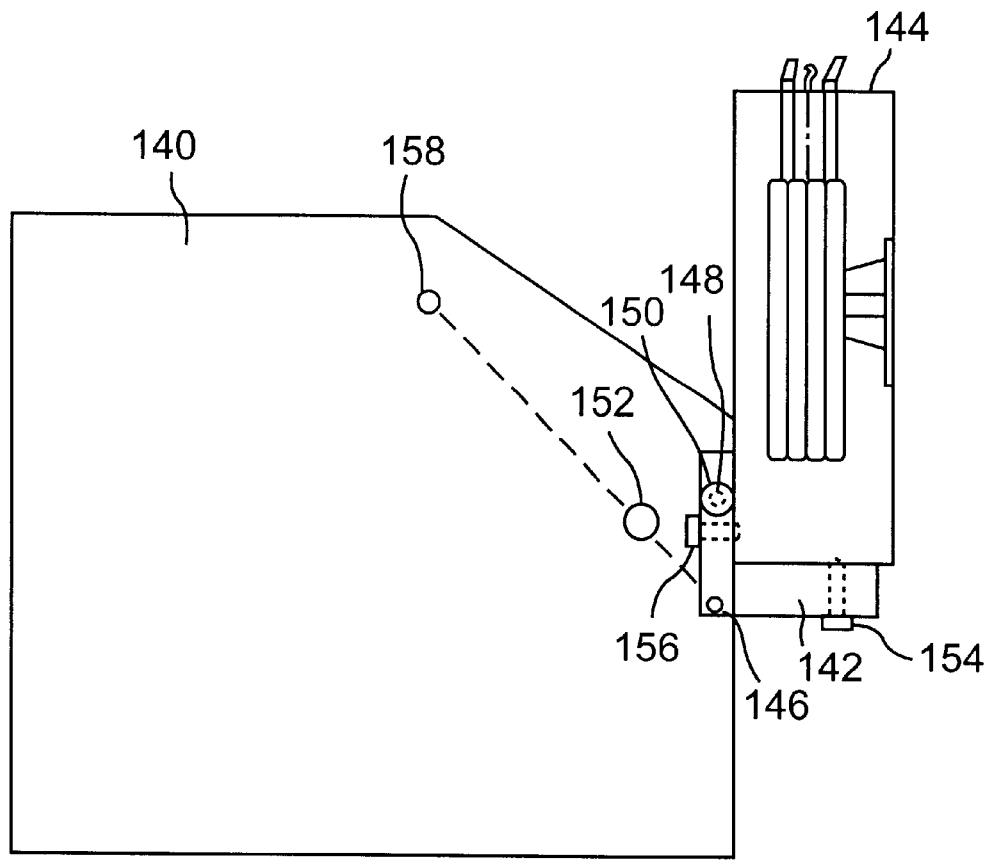
FIG. 18 is a side view of an adjustable container frame with the container in a firs position.
Figure 19:
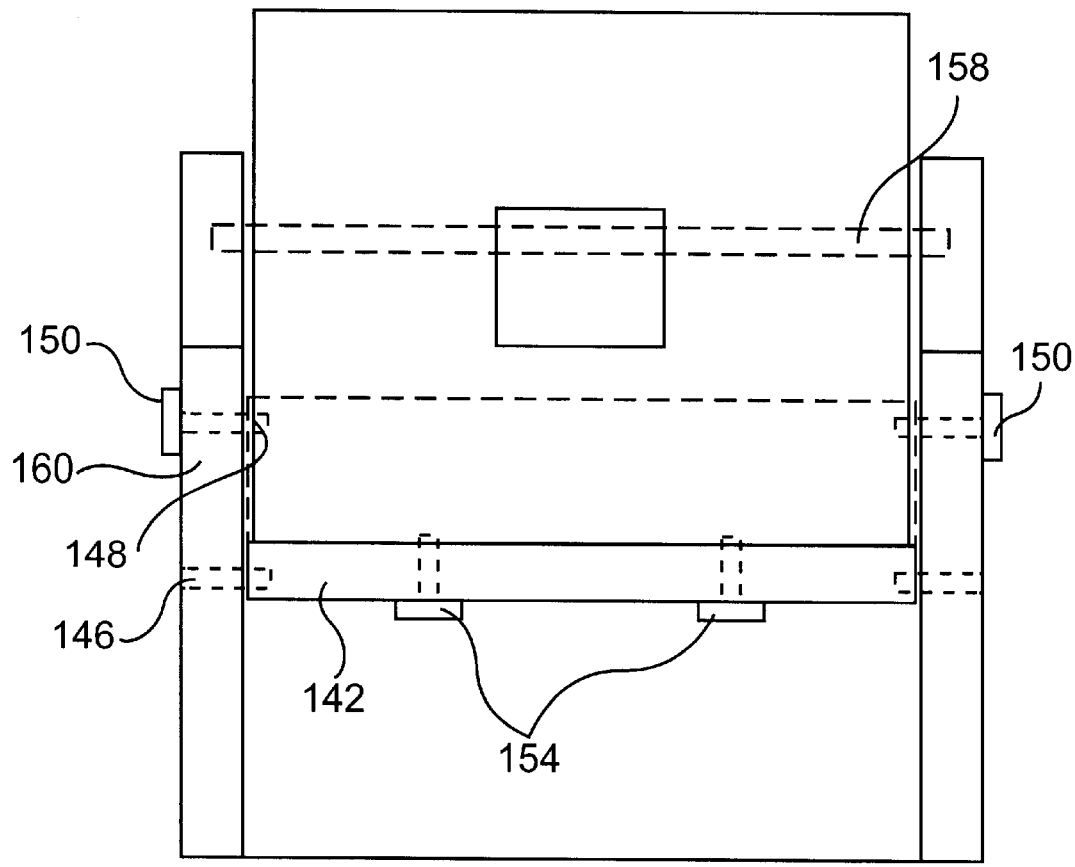
FIG. 19 is a front view of the adjustable container frame of FIG. 18.
Figure 20:
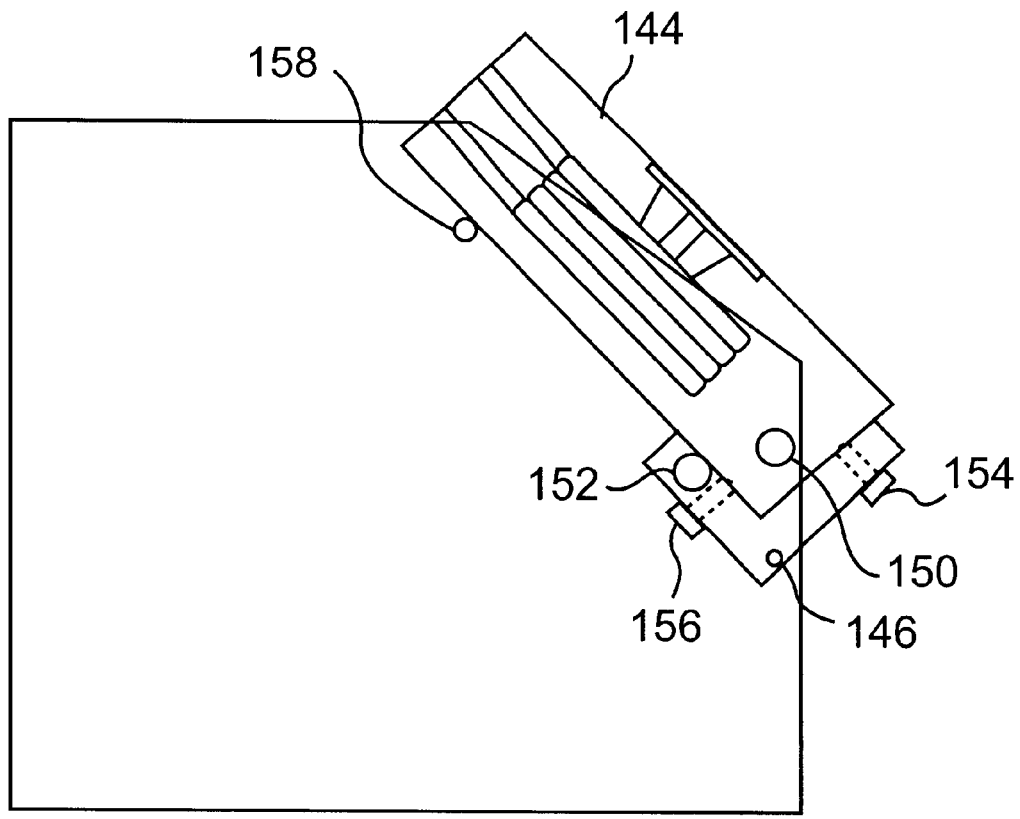
FIG. 20 is a side view of the adjustable container frame of FIG. 18 with the container in a second position.

In accordance with the present invention, the containers of the first and second embodiments may be mounted in a container frame so that the angle of the fabric sample holder may be varied. As previously discussed, the angle of the fabric in a standard U.S. flammability test is 45 degrees relative to the horizontal, whereas the angle of the fabric in a standard U.K. flammability test is 90 degrees relative to the horizontal (i.e., vertical). It is advantageous to have an apparatus in which the flammability of a fabric can be tested at both of these angles. In the illustrated apparatus of FIGS. 18–20, a container frame 140 is provided so that the angle of a fabric relative to the horizontal can be set at either approximately 45 degrees or approximately 90 degrees (vertical). In the example shown in FIG. 18, the container 140 includes a pivot structure 142 on which the container 144 is mounted. In the example shown in FIGS. 18–20, the pivot structure 142 is made of two rectangular portions that are attached at ninety degree angles to each other. The pivot structure 142 pivots about pivot pins 146. The pivot pins 146 pass from the side walls 160 of the container frame 140 into the pivot structure 142. The container 144 is positioned on the pivot structure and attached to the pivot structure by screws 154 and 156. Although screws are shown in FIGS. 18–20, any other type of fastener is also acceptable. In order to position the container in the vertical position as shown in FIGS. 18–19, pins 150 are provided for insertion into pin holes 148 of the pivot structure. Each pin 150 axially slides relative to side wall 160 of the container frame. In order to pivot the container to the 45 degree angle as shown in FIG. 20, each pin 150 is retracted from the corresponding pin hole 148 of the container, and the pivot structure and container are pivoted towards 45 degrees. When the pins 152 align with the pin holes 148, the pins 152 are inserted into the pin holes. At this position, the container 144 will be supported against rod 158 as shown in FIG. 20. Other arrangements are also possible where, for example, the fabric can be positioned at a horizontal position, or at a wider range of angular positions.

The provision of an adjustable angular position allows each fabric sample to be tested at different angular orientations. This is particularly advantageous when calculating for flame speed and flame spread patterns. For a given fabric, maximum flame spread speed is noted for upward burning at the substantially vertical orientation, with slightly lower speeds at a substantially 45 degree angle, and much lower speeds at a substantially horizontal orientation.

The operation of the apparatus will be described below. After placing a piece of fabric or other material in the fabric sample holder at the selected angle, water having a temperature substantially the same as the temperature of normal human skin is circulated through the heat exchange coil. This circulation of water through the heat exchange coil transfers heat to the fluid in the container, thereby maintaining the temperature of the fluid in the container at a regulated temperature. After the appropriate temperature for the fluid has been obtained, the fabric is ignited. The ignition time is recorded, as well as the burn time over the length of the sample. The temperatures measured by the thermocouples throughout the burning of the fabric and the cooldown are recorded using the data acquisition system. A graph of the temperature values of given fabrics over the burning period are shown for example in FIGS. 25–28. In FIGS. 25–28, each line represents a different thermocouple position.

Figure 24:
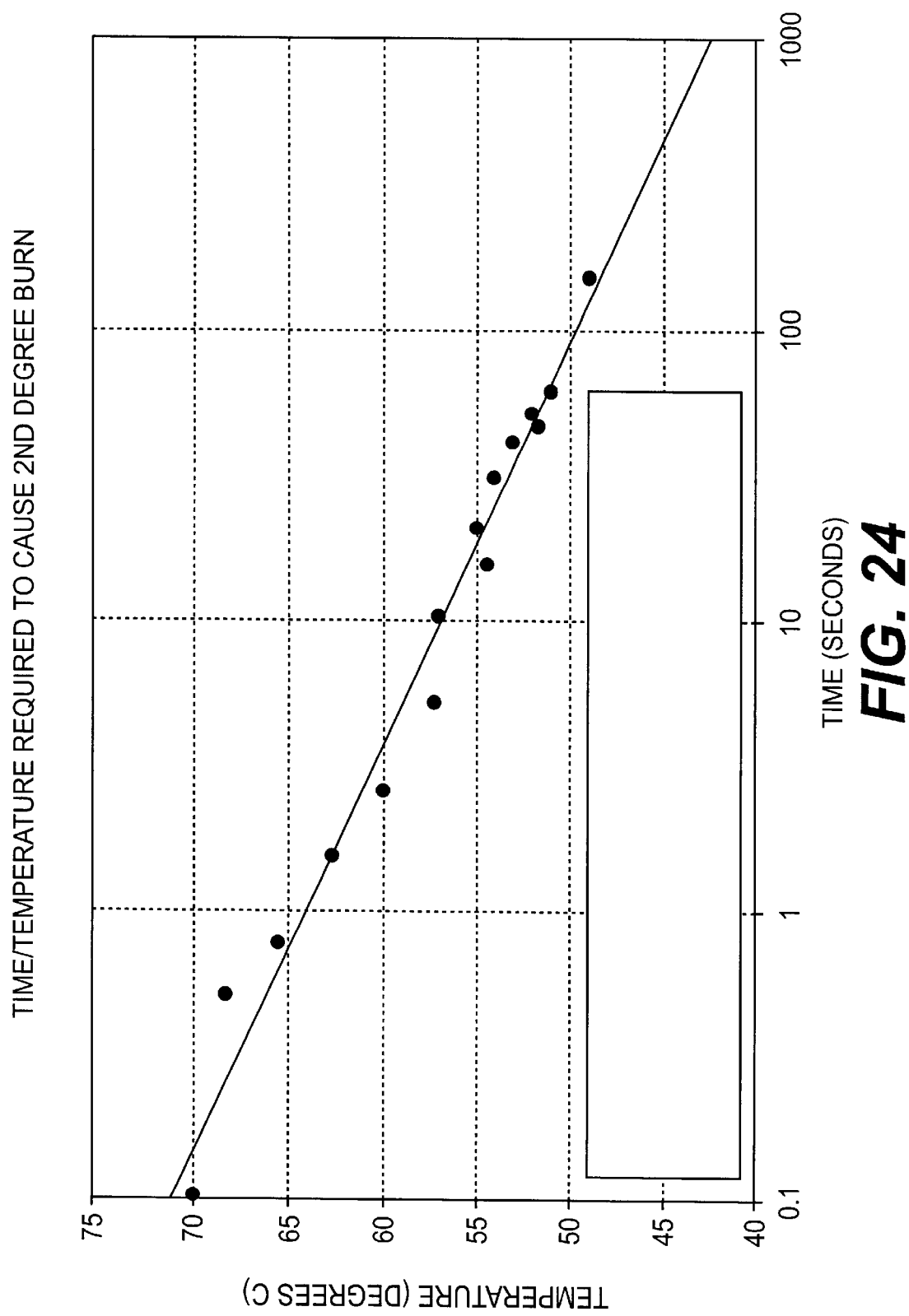
FIG. 24 is a graph of a time-temperature burn threshold for human skin.
Figure 25:
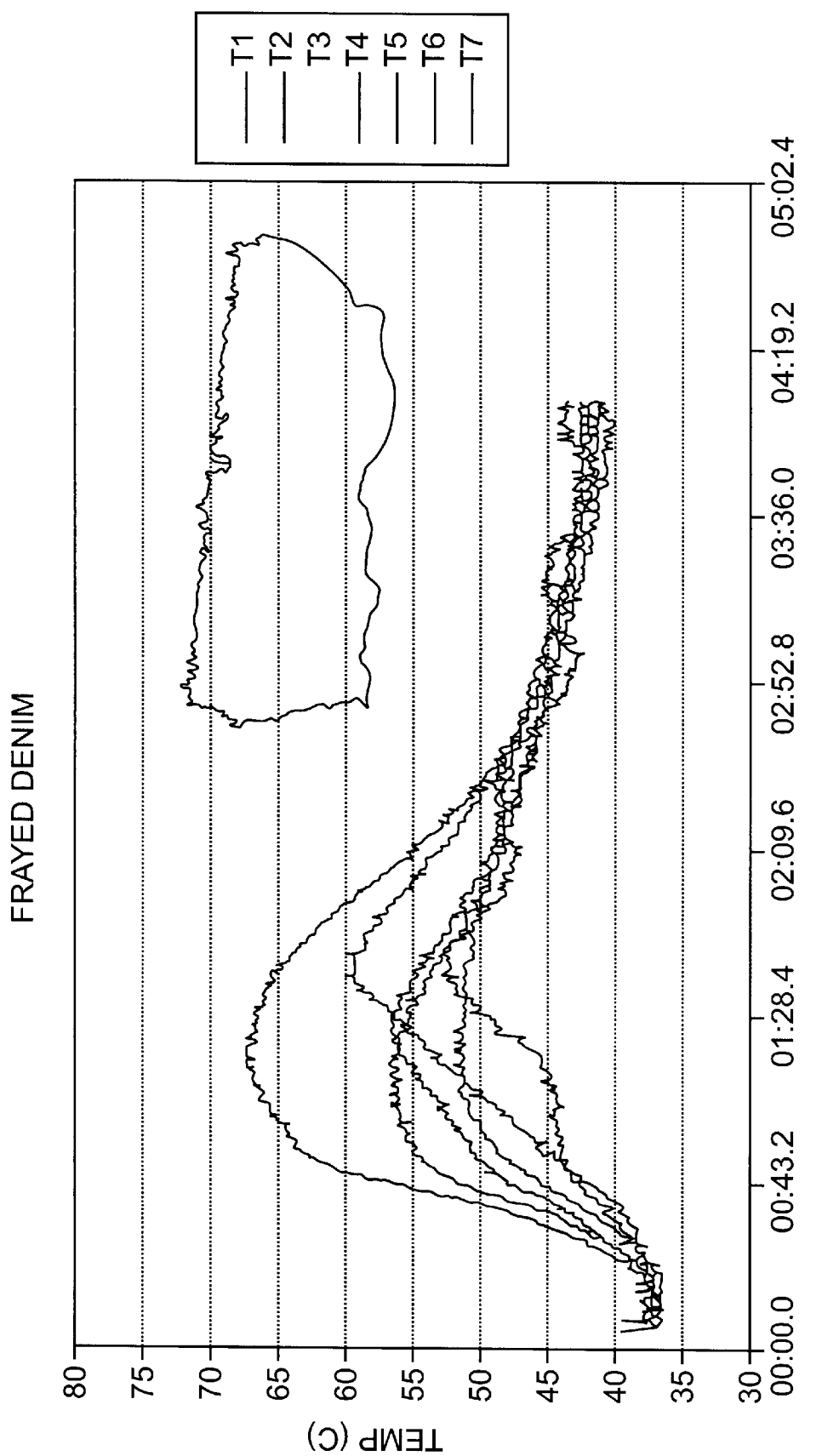
FIGS. 25–28 are examples of temperature measurements for flammability tests for a variety of materials.
Figure 26:
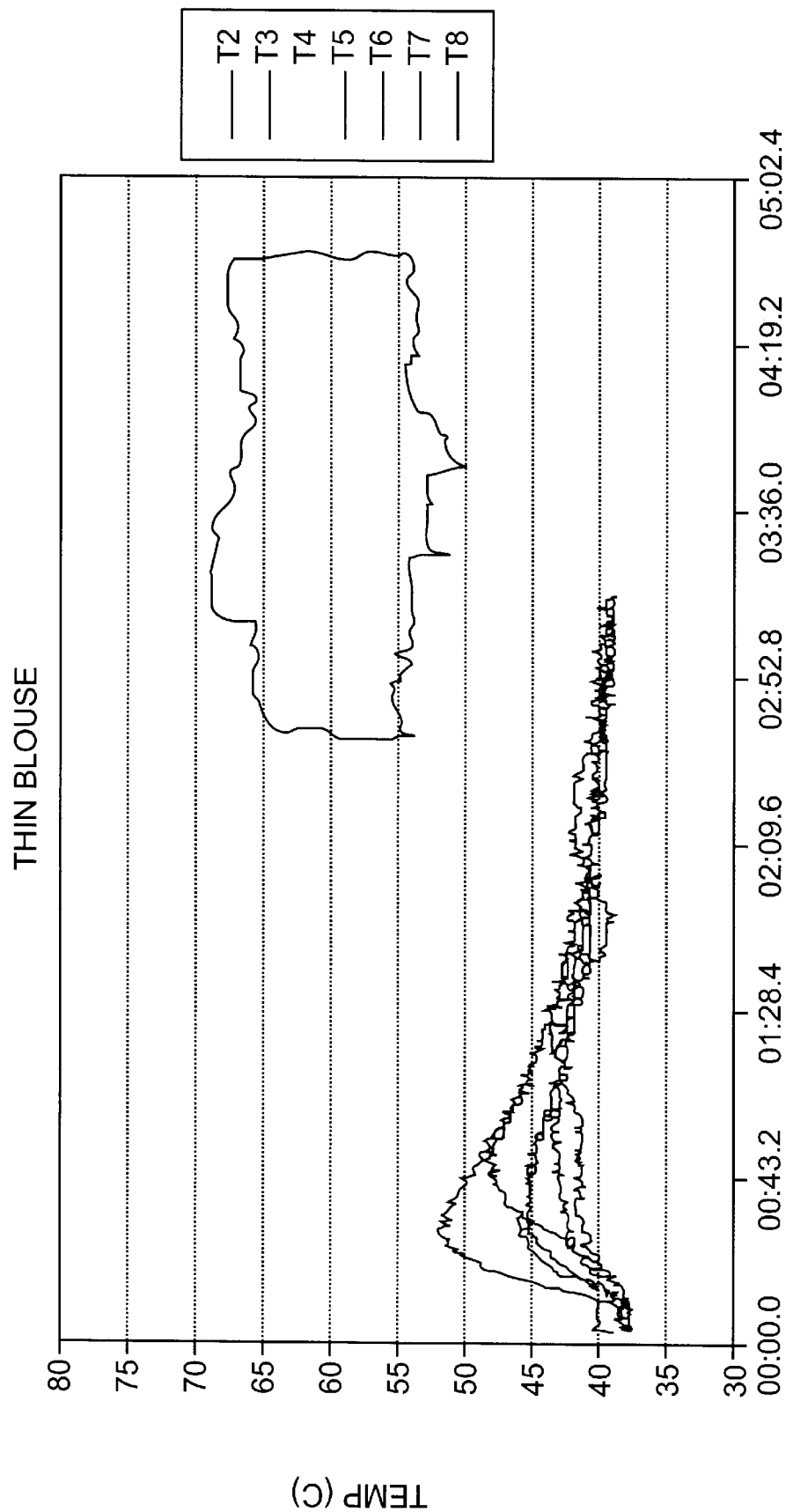
Figure 27:
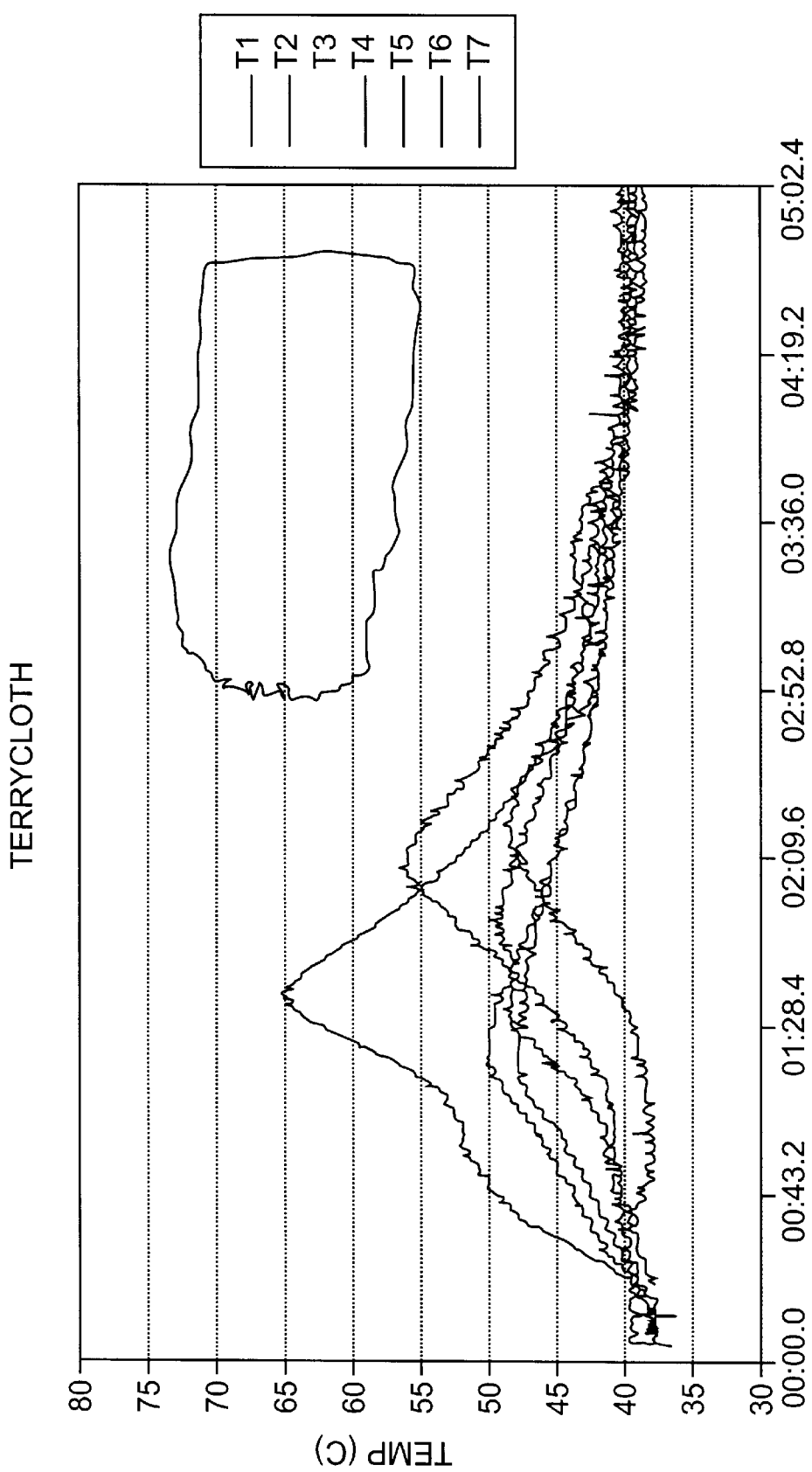
Figure 28:
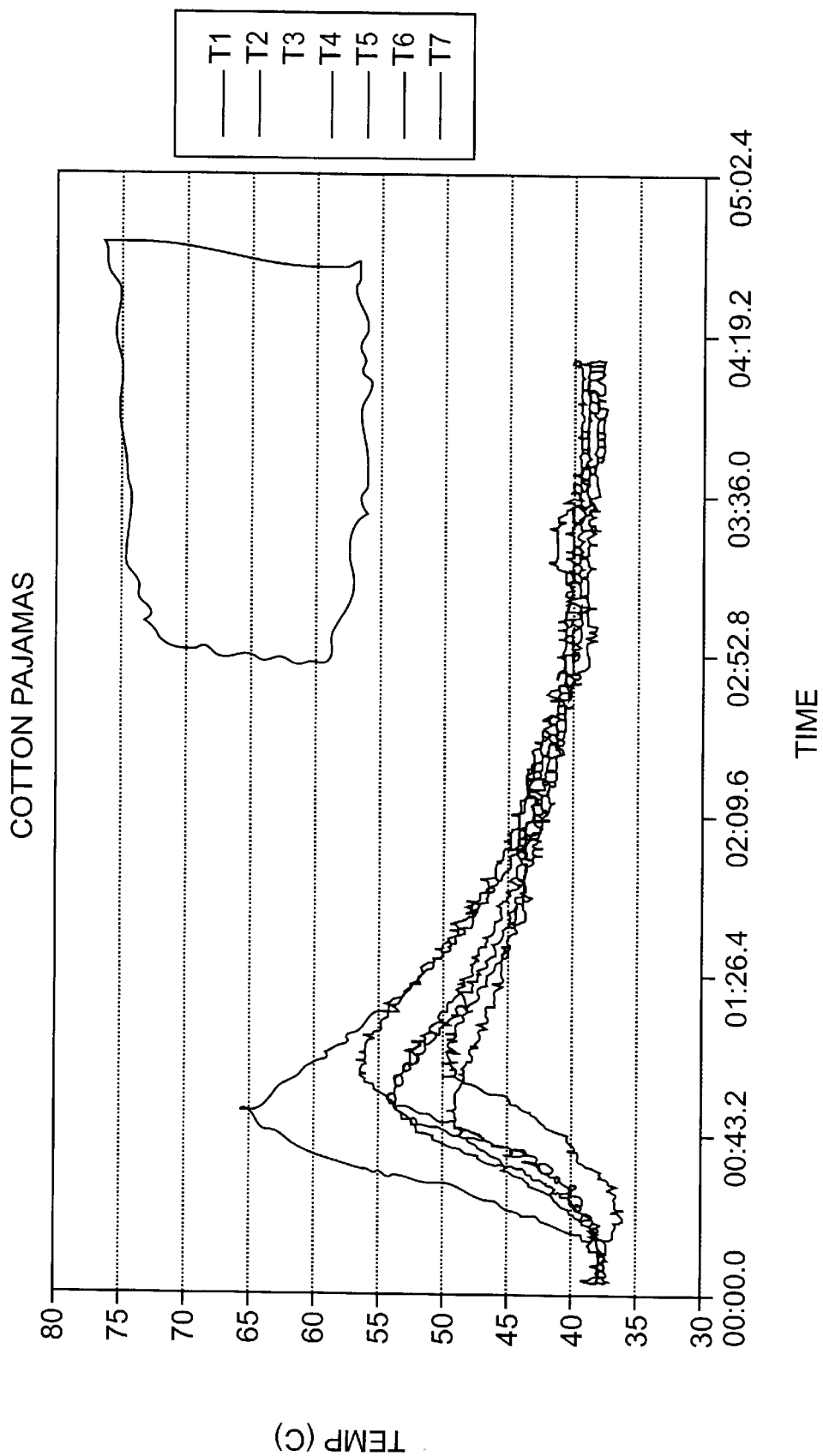
Figure 29:
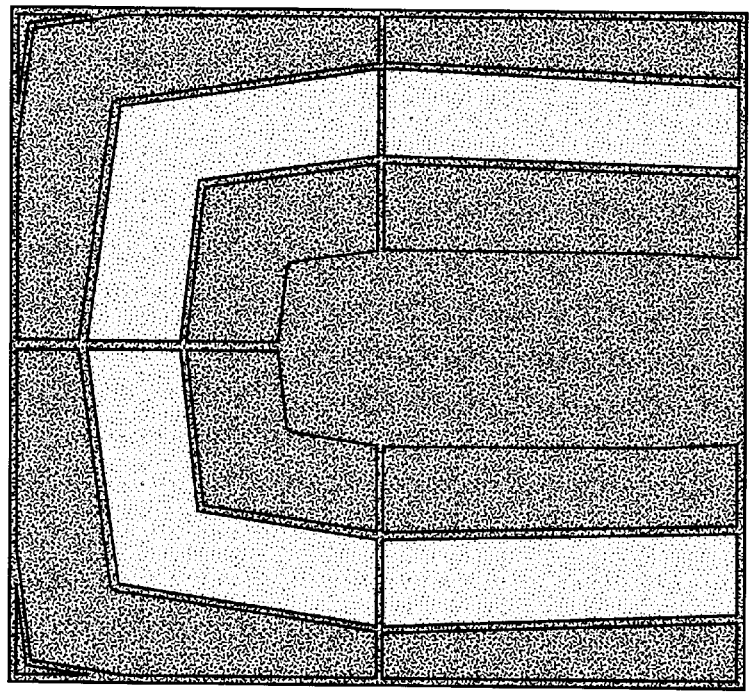
Figure 29:
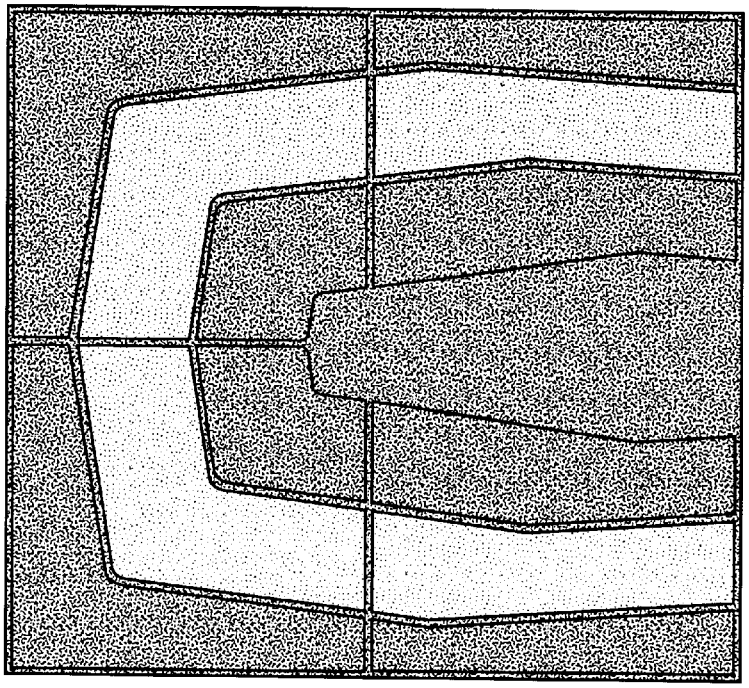
Figure 30:
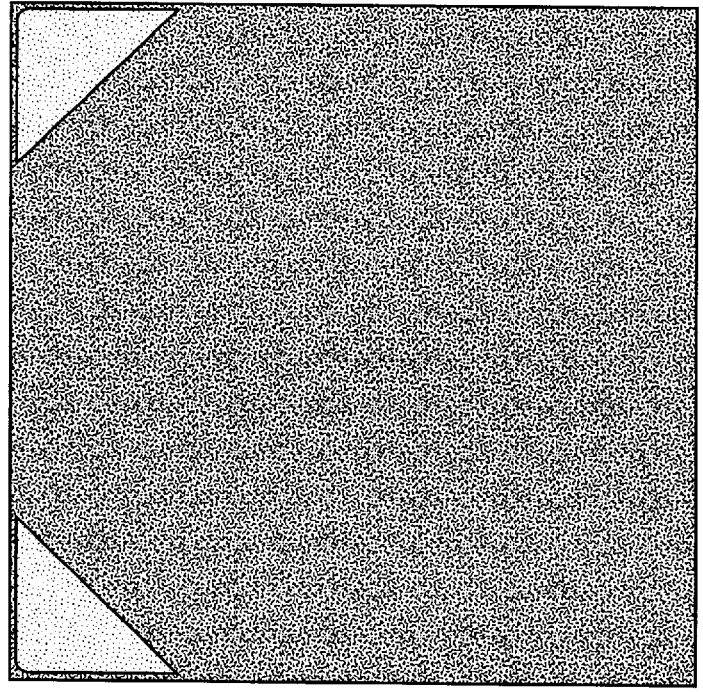
Figure 30:
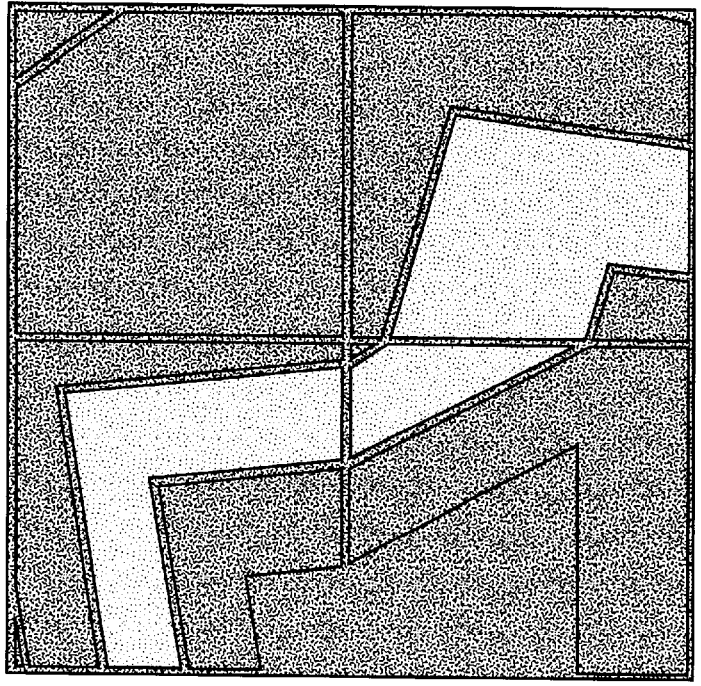
Figure 31:
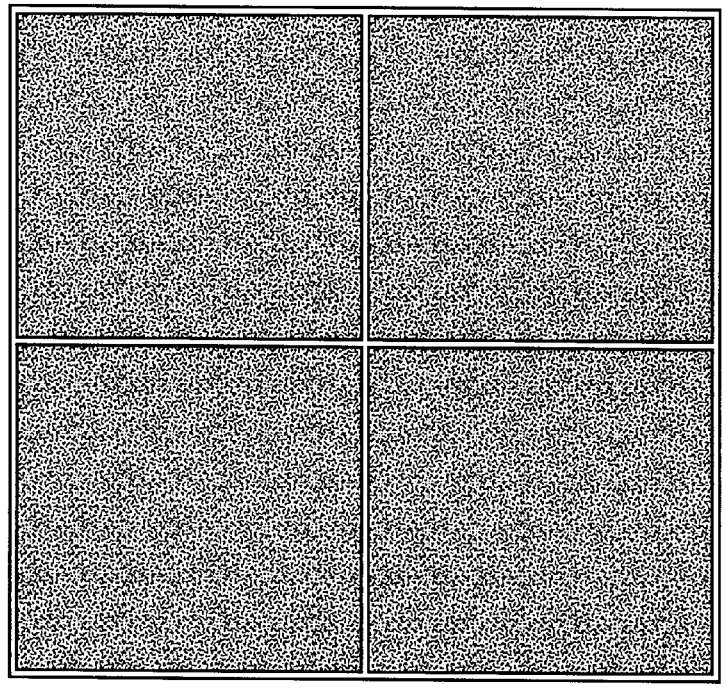
Figure 31:
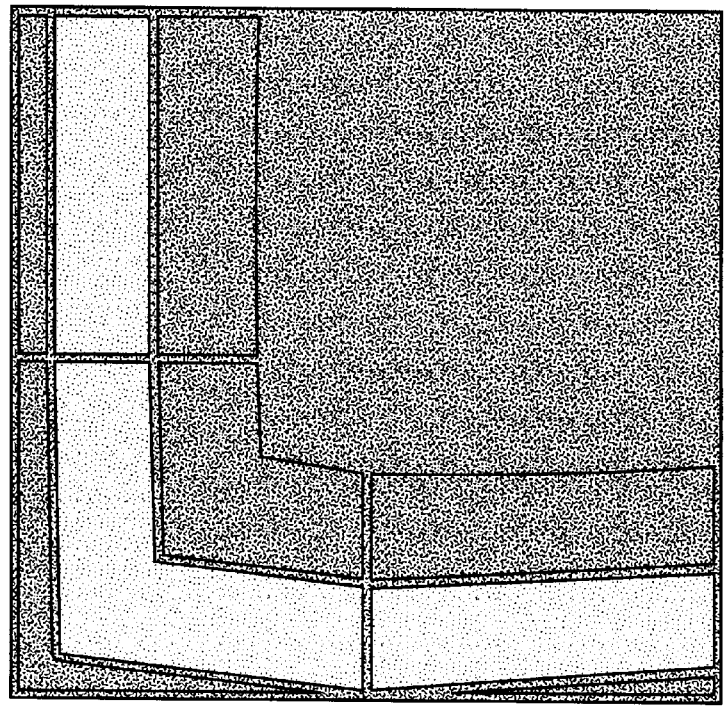

The procedure for analyzing the test data will be described below. Given the burn time, the burn rate (inches/second or metric equivalent) can be calculated. A burn injury index value can then be calculated based on the temperatures which were reached during the test and the amount of time that the artificial human skin was at the temperatures. The time and temperature required to cause second degree burns has been calculated. FIG. 24 shows a graph of the time and temperature required to cause second degree burns. The equation of this curve is TEMP=−3.0929 Ln(TIME)+ 63.902, where TEMP=Skin Temperature (deg. C.); TIME= Exposure Time (seconds). The curve fit is $R^2$=0.9776. As shown on this graph, if the temperature of the skin stays below 40 deg. C., it would take an almost infinite amount of time for a second degree burn to occur. On the other hand, if the temperature raises above 60 degrees, a second degree burn will occur almost instantaneously. The analysis below will only be used for temperatures in the range of 40 to 60 degrees C.

The amount of time that the sensor plate is above each 5 degree C. increment between 40 and 60 degrees is recorded. For each increment and time above the increment, a corresponding burn value is calculated. These burn values are added up for the entire flammability test to obtain a total burn index value of 0.0 to 1.0 for each thermocouple.

Once each thermocouple has been assigned a burn injury index value, a burn map is calculated. The burn map will show the index injury at each of the locations for the thermocouples. Burn maps are shown for example as FIGS. 29–32. In the burn map, each different shading represents a burn injury index value in 0.2 increments. For example, in the burn maps shown in FIGS. 29–32, a first color represents burn injury index of 0.0 to 0.2, a second color represents a burn injury index of 0.2 to 0.4, a third color represents a burn injury index of 0.4 to 0.6, a fourth color represents a burn injury index of 0.6 to 0.8, and a fifth color represents a burn injury index value of 0.8 to 1.0.

The burn maps in FIGS. 29–32 show burn index values for 45 degree and vertical positions for the fabric samples. The United States standards for clothing and textiles are based on an orientation of 45 degrees, ignition times of 1 second or less, and a maximum burn rate of 1.5 inch/second. The British standards for sleepwear are based on a vertical orientation, ignition times of 10 seconds or less, and a maximum burn rate of 0.5 inch/second. Therefore, it is important to have a test apparatus that can measure the flammability characteristics at both orientations.

After calculating the burn index map, the maximum burn injury index value is recorded. An average burn injury index value can also be calculated. This is an average of the burn injury index values for all of the thermocouple positions.

Figure 22:
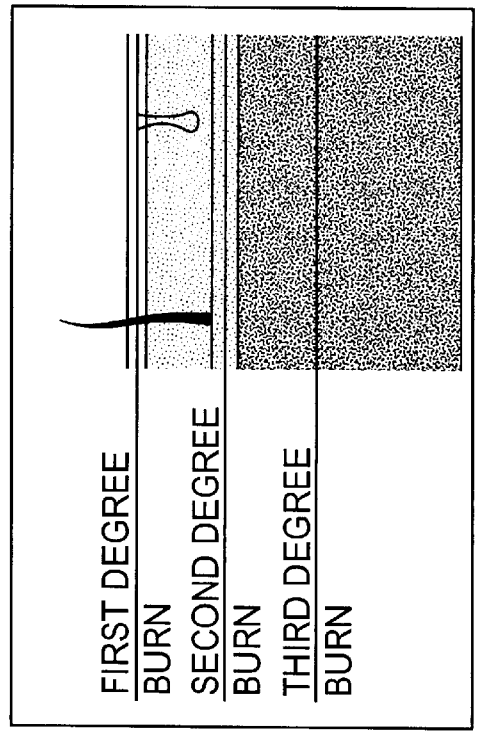
FIG. 22 is a schematic of layers of human skin.

The apparatus and method described allow for a calculation of the amount of burn caused by a particular fabric to underlying human tissue, e.g., skin. As shown in FIG. 22, there are varying degrees of burns on the skin. First degree burns are referred to as surface burns. These are minor burns which heal quickly. Second degree burns are referred to as partial-thickness burns. These are serious injuries which require medical attention and often require skin-grafts to aid in the healing process. Third degree burns are referred to as full-thickness burns. These injuries are very severe and require immediate medical attention. Fourth degree burns are referred to as penetrating burns. These injuries are characterized by damage to bones and internal organs.

The thermocouples must be placed at a certain depth from the top of the sensor plate in order to replicate the human skin. Human skin possesses a very limited thickness. Adult skin can be more than 5 mm on the back, but as little as 0.5 mm on the eyelids. Average skin thickness is about 1–2 mm. These measurements are approximately halved in children. Therefore, the thermocouple should be placed at a depth appropriate for the type of skin which is being measured.

A brief discussion of the characteristics and principles of flammability will further clarify the purpose of the above described apparatus and method. When a fabric is exposed to a heat source, it will experience a temperature rise under the influence of the resultant heat transfer. If the temperature of the source is high enough and the net rate of heat transfer to the fabric is great, pyrolitic decomposition of the fiber substrates will soon occur. The products of this decomposition will include combustible gases, noncombustible gases, and carbonaceous char. The combustible gases mix with ambient oxygen and if its composition and the temperature are favorable, the mixture will ignite, yielding a flame. Part of the heat generated within the flame is transferred to the fabric to sustain the burning process and part is lost to the surroundings, i.e., the underlying skin.

Figure 21:
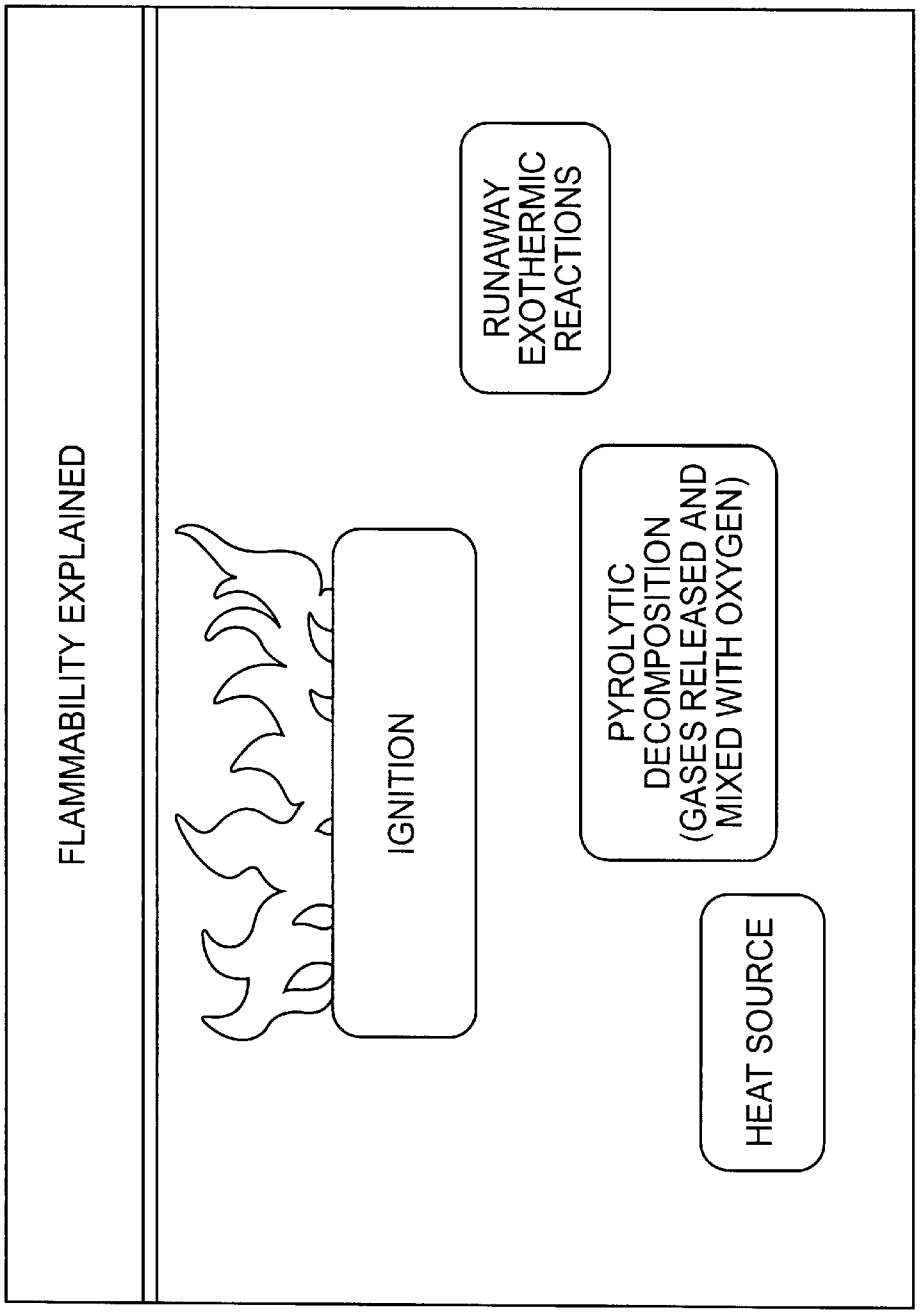
FIG. 21 is schematic explaining the fundamentals of flammability.

As illustrated in FIG. 21, when a fabric is exposed to an ignition source, four possible results can occur. A first possibility is that the fabric does not ignite and gases formed by pyrolosis of the fibers do not burn in the igniting flame. A second possibility is that the fabric does not ignite, but the gases formed do burn in the igniting flame. A third possibility is that the fabric ignites, but burns for only a short interval after removal of the igniting flame. A fourth possibility is that the fabric ignites and continues to burn after removal of the igniting flame. Once a fabric has been ignited, the flame may spread throughout the fabric at a variety of speeds and in a variety of patterns. Factors which may affect the characteristics of flame spread in a fabric include: fiber composition, fabric orientation, fabric weight-per-unit area, the amount of space between the fabric and the body, and surface characteristics of the fabric (i.e., are the edges of the fabric exposed). The composition of the fabric is the main factor. For example, non-thermoplastic fabrics will usually ignite and continue to burn, while thermoplastic fabrics will often shrink away from a flame, thereby hindering ignition, or may melt after ignition, often causing the fabric to self-extinguish before the flame can spread. As previously discussed, the angle of the fabric also effects the flame spread characteristics of a given fabric.

The apparatus and method of the present invention allow for these various factors to be taken into account when assessing burn injury to underlying tissue from a flammable material.

It will be apparent to those skilled in the art that various modifications and variations can be made in the apparatus and method for assessing burn injury to underlying tissue from a flammable material, use of the apparatus of the present invention, and in construction of this apparatus, without departing from the scope or spirit of the invention.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An apparatus for assessing burn injury to underlying tissue from a flammable material, comprising:
   an artificial human tissue;
   a plurality of temperature sensors located at predetermined locations in the artificial human tissue to measure temperature of the artificial human tissue during a flammability test; and
   a data acquisition system receiving the temperature readings from the plurality of
   temperature sensors and calculating a burn injury index value.

2. The apparatus of claim 1, wherein said artificial human tissue comprises a plate of material having thermal properties similar to that of ordinary human skin, said plate having a top surface and a bottom surface.

3. The apparatus of claim 2, wherein said material having thermal properties similar to that of ordinary human skin includes mica.

4. The apparatus of claim 2, wherein said plurality of temperature sensors are embedded in said plate below said top surface so that said sensors do not completely pass through said plate.

5. The apparatus of claim 4, further comprising a heat sink device for simulating the heat sink properties of a human body.

6. The apparatus of claim 5, wherein said heat sink device includes a container filled with a fluid, said plate comprising at least a portion of a wall of said container.

7. The apparatus of claim 6, further comprising a frame for supporting said container and plate, said frame including adjustment means for adjusting an angle of a top surface of the plate.

8. The apparatus of claim 6, wherein said heat sink device further includes a heat exchanger for exchanging heat with said fluid in said container, said heat exchanger having a second fluid therein with a temperature substantially the same as a normal temperature of human skin.

9. The apparatus of claim 8, further comprising a fluid supply system for supplying said second fluid to said heat exchanger, said supply system including a reservoir for said second fluid, a heater for maintaining said second fluid at a constant temperature, and a pump.

10. The apparatus of claim 8, wherein said heat exchanger is a heat exchange coil.

11. The apparatus of claim 1, wherein said data acquisition system calculates a burn rate in addition to the burn injury index value.

12. The apparatus of claim 1, further comprising a flammable material sample holder for holding a flammable material sample at a predetermined distance from the sensor plate, wherein said fabric material sample holder includes at least one spacer for adjusting the distance between the fabric material sample and the sensor plate.

13. An apparatus for assessing burn injury to underlying tissue from a flammable material comprising:
   artificial human tissue having thermal properties similar to that of ordinary human skin;
   a heat sink device for simulating heat sink properties of a human body;
   a plurality of temperature sensors located at predetermined locations in the artificial human tissue to measure temperature of the artificial human tissue during a flammability test; and
   a data acquisition system receiving the temperature readings from the plurality of temperature sensors and calculating a burn injury index value.

14. The apparatus of claim 13, wherein said heat sink device includes a container filled with a first fluid at a regulated temperature.

15. The apparatus of claim 14, wherein said artificial human tissue is located in an opening on a wall of the container and comes in direct contact with the first fluid.

16. The apparatus of claim 15, wherein said heat sink device further includes a heat exchanger having a second fluid therein with a temperature substantially the same as the normal temperature of human skin.

17. The apparatus of claim 16, further comprising a fluid supply system for supplying said second fluid to said heat exchanger, said supply system including a reservoir for said second fluid, a heater for maintaining said second fluid at a constant temperature, and a pump.

18. The apparatus of claim 13, wherein said artificial human tissue comprises a plate mounted on said heat sink device.

19. The apparatus of claim 18, wherein said plate is composed of mica.

20. An apparatus for assessing burn injury to underlying tissue from a flammable material, comprising:

artificial human tissue in the form of a plate of material having thermal properties similar to that of ordinary skin;

a heat exchange tank for maintaining said artificial human tissue at a regulated temperature, said heat exchange tank substantially filled with a fluid, said artificial human tissue being mounted in an opening in said heat exchange tank and being contacted on an interior surface by said fluid;

heat exchanger for exchanging heat with said fluid in said heat exchange tank to maintain said fluid of the said exchange tank at said regulated temperature;

a plurality of temperature sensors located at predetermined locations in said artificial human tissue to measure a temperature of said artificial human tissue during a flammability test;

a water supply device for supplying water to the interior of the heat exchanger, said water supply device including a water tank, a pump, and a heater; and a data acquisition system attached to said plurality of temperature sensors for recording the temperature of said artificial human tissue and calculating a burn injury index value.

21. A method for assessing burn injury to underlying tissue from a flammable material during a flammability test, comprising the steps of:

mounting a sample of flammable material at a selected distance from an artificial human tissue located on a test apparatus;

circulating a fluid through said test apparatus at a temperature substantially the same as ordinary human skin temperature;

performing a flammability test; and recording temperature of the artificial human tissue at a plurality of locations over predetermined intervals during the flammability test and calculating a burn injury index value.

22. The method of claim 21, further comprising the step of calculating a burn rate for the respective flammable material.

23. The method of claim 22, further comprising the step of adjusting the distance of the flammable material from the sensor plate and performing additional flammability tests.

24. The method of claim 21, further comprising the step of determining a pattern of burning of the flammable material.

25. The method of claim 21, further comprising the step of assigning a burn value for each of the plurality of locations where temperatures are recorded.

26. The method of claim 25, wherein the burn value is calculated as a function of the temperatures recorded during the flammability test, and an amount of time the artificial tissue is at each temperature.

27. The method of claim 21, further comprising calculating a burn rate.

28. The method of claim 21, further comprising determining a time and a temperature to cause a second degree burn to the artificial human tissue.

* * * * *

UNITED STATES PATENT AND TRADEMARK OFFICE
CERTIFICATE OF CORRECTION

PATENT NO. : 6,312,155 B1  Page 1 of 1
DATED : November 6, 2001
INVENTOR(S) : Daniel Stool et al.

It is certified that error appears in the above-identified patent and that said Letters Patent is hereby corrected as shown below:

<u>Column 13, claim 20,</u>
Line 12, "heat exchanger" should read -- a heat exchanger --.

Signed and Sealed this

Twenty-sixth Day of March, 2002

Attest:

Attesting Officer

JAMES E. ROGAN
*Director of the United States Patent and Trademark Office*